US012570604B2

(12) United States Patent
Zhang et al.

(10) Patent No.: US 12,570,604 B2
(45) Date of Patent: Mar. 10, 2026

(54) POLYMORPHIC FORMS OF A TETRACYCLINE COMPOUND AND USES THEREOF

(71) Applicant: Tetraphase Pharmaceuticals, Inc., Watertown, MA (US)

(72) Inventors: Wu-Yan Zhang, Lexington, MA (US); Minsheng He, Andover, MA (US)

(73) Assignee: Tetraphase Pharmaceuticals, Inc., Waltham, MA (US)

( * ) Notice: Subject to any disclaimer, the term of this patent is extended or adjusted under 35 U.S.C. 154(b) by 1164 days.

(21) Appl. No.: 17/292,295

(22) PCT Filed: Nov. 8, 2019

(86) PCT No.: PCT/US2019/060449

§ 371 (c)(1),
(2) Date: May 7, 2021

(87) PCT Pub. No.: WO2020/097450

PCT Pub. Date: May 14, 2020

(65) Prior Publication Data

US 2021/0395198 A1 Dec. 23, 2021

Related U.S. Application Data

(60) Provisional application No. 62/758,210, filed on Nov. 9, 2018.

(51) Int. Cl.
*C07D 207/16* (2006.01)

(52) U.S. Cl.
CPC ........ *C07D 207/16* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 8,501,716 | B2 | 8/2013 | Zhou et al. |
| 8,796,245 | B2 | 8/2014 | Zhou et al. |
| 8,906,887 | B2 | 12/2014 | Zhou et al. |
| 10,961,190 | B2 | 3/2021 | LaFrance et al. |
| 11,578,044 | B2 | 2/2023 | LaFrance et al. |
| 12,269,807 | B2 | 4/2025 | LaFrance et al. |

FOREIGN PATENT DOCUMENTS

| | | | |
|---|---|---|---|
| WO | WO-2010/017470 | A1 | 2/2010 |
| WO | WO-2018/051102 | A1 | 3/2018 |
| WO | WO-2018/075767 | A1 | 4/2018 |
| WO | WO-2020/097450 | A1 | 5/2020 |

OTHER PUBLICATIONS

Clark et al., Journal of Medicinal Chemistry, 2012, 55, 606-622. (Year: 2012).*

Grossman et al., "Fluorocycline TP-271 Is Potent against Complicated Community-Acquired Bacterial Pneumonia Pathogens," mSphere, 2(1):1-11 (2017).

International Search Report and Written Opinion for International Application No. PCT/US19/60449 dated Jan. 29, 2020.

* cited by examiner

*Primary Examiner* — Sarah Pihonak
*Assistant Examiner* — Donna M Nestor
(74) *Attorney, Agent, or Firm* — Foley Hoag LLP

(57) ABSTRACT

The invention relates to crystalline forms of the bis-HCl salt of a compound represented by Structural Formula (1), and pharmaceutical compositions comprising crystalline forms of the bis-HCL salt of a compound represented by Structural Formula (1) described herein. The crystalline forms of the bis-HCl salt of a compound of Structural Formula (1) and compositions comprising the crystalline forms of the compound of Structural Formula (1) provided herein, in particular, crystalline Form A, crystalline Form B, crystalline Form C, and crystalline Form D, or mixtures thereof, can be incorporated into pharmaceutical compositions, which can be used to treat various disorders. Also described herein are methods for preparing the crystalline forms (e.g., Forms A, B, C and D) of the bis-HCl salt of a compound represented by Structural Formula (1).

(1)

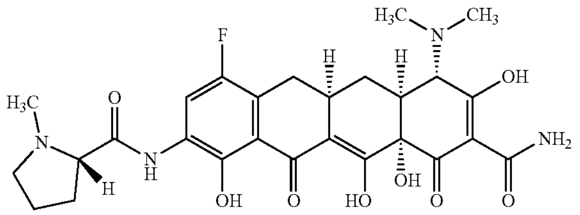

40 Claims, 16 Drawing Sheets

POLYMORPHIC FORMS OF A TETRACYCLINE COMPOUND AND USES THEREOF

RELATED APPLICATIONS

This application is the U.S. National Stage of International Application No. PCT/US2019/060449, filed Nov. 8, 2019, which designates the U.S., published in English. and claims the benefit of U.S. Provisional Application No. 62/758,210, filed on Nov. 9, 2018. The entire teachings of the above applications are incorporated herein by reference.

GOVERNMENT SUPPORT

This invention was made with government support under Contract No. HHSO100201200002C and Subcontract No. 7834S1 awarded by the Department of Health and Human Services. The government has certain rights in the invention.

BACKGROUND OF THE INVENTION

The tetracyclines are broad spectrum anti-microbial agents that are widely used in human and veterinary medicine. The total production of tetracyclines by fermentation or semi-synthesis is measured in the thousands of metric tons per year.

The widespread use of tetracyclines for therapeutic purposes has led to the emergence of resistance to these antibiotics, even among highly susceptible bacterial species. Tetracycline analogs having improved antibacterial activities and efficacies against other tetracycline responsive diseases or disorders have been described (see, for example, U.S. Pat. No. 8,796,245). A particularly useful compound is (S)—N-((5aR,6aS,7S,10aS)-9-carbamoyl-7-(dimethylamino)-4-fluoro-1,8,10a,11-tetrahydroxy-10,12-dioxo-5,5a,6,6a,7,10,10a,12-octahydrotetracen-2-yl)-1-methylpyrrolidine-2-carboxamide, which has the chemical structure shown in Structural Formula 1:

(1)

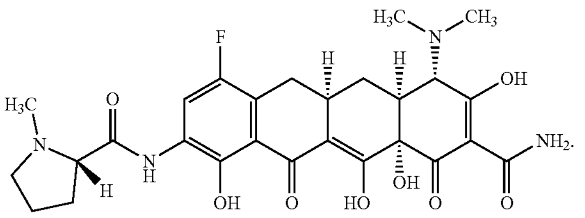

The solid form of a compound can be important in the formulation of pharmaceutical compositions. For example, crystalline and amorphous forms of a compound can have different physical properties (e.g., stability, dissolution rate, density, etc.) relating to their suitability for use in pharmaceutical compositions. The difference in physical properties can also affect a crystalline or amorphous form's usefulness, for example, as an intermediate in the synthesis of a form suitable for use in pharmaceutical compositions.

There is a need for crystalline forms of compound of Structural Formula 1 that are thermodynamically stable and suitable for use in pharmaceutical compositions (e.g., are readily dissolvable, exhibit good flow properties and/or good chemical stability). There is a further need for crystalline forms of compound of Structural Formula 1 having physical properties that enable the manufacture of compound of Structural Formula 1 for use in pharmaceutical compositions in high yield and high purity.

SUMMARY OF THE INVENTION

The present invention relates to crystalline forms of the bis-HCl salt of the compound represented by Structural Formula 1, designated crystalline Form A, crystalline Form B, crystalline Form C, and crystalline Form D and compositions comprising the crystalline forms.

In one embodiment, a crystalline form of a compound represented by the bis-HCl salt of Structural Formula 1 is provided, wherein the crystalline form is Form A. In this embodiment, crystalline Form A is characterized by at least three x-ray powder diffraction peaks at 2θ angles selected from 7.32°, 8.91°, 10.15°, and 10.57°.

In another embodiment, a crystalline form of a compound represented by bis-HCl salt of Structural Formula 1 is provided, wherein the crystalline form is Form B. In this embodiment, crystalline Form B is characterized by at least three x-ray powder diffraction peaks at 2θ angles selected from 5.72°, 10.73°, 12.34°, and 16.89°.

In yet another embodiment, a crystalline form of a compound represented by the bis-HCl salt of Structural Formula 1 is provided, wherein the crystalline form is Form C. In this embodiment, crystalline Form C is characterized by at least three x-ray powder diffraction peaks at 2θ angles selected from 6.02°, 11.14°, 12.95°, and 18.57°.

In another embodiment, a crystalline form of a compound represented by the bis-HCl salt of Structural Formula 1 is provided, wherein the crystalline form is Form D. In this embodiment, crystalline Form D is characterized by at least three x-ray powder diffraction peaks at 2θ angles selected from 3.68°, 13.26°, 16.11°, and 16.97°.

Another embodiment is a pharmaceutical composition comprising particles of Form A, Form B, Form C, Form D or mixtures thereof and a pharmaceutically acceptable carrier.

A further embodiment is a method for treating or preventing a tetracycline-responsive disease or disorder, the method comprising administering to a subject in need thereof a therapeutically or prophylactically effective amount of crystalline Form A, Form B, Form C, Form D or a mixture thereof or a pharmaceutical composition comprising particles of Form A, Form B, Form C, Form D or mixtures thereof and a pharmaceutically acceptable carrier. In one aspect, the tetracycline-responsive disease or disorder is an infection. In a specific aspect, the infection is caused by bacteria.

BRIEF DESCRIPTION OF THE DRAWINGS

The foregoing will be apparent from the following more particular description of example embodiments of the invention.

DETAILED DESCRIPTION OF THE INVENTION

Figure 1:
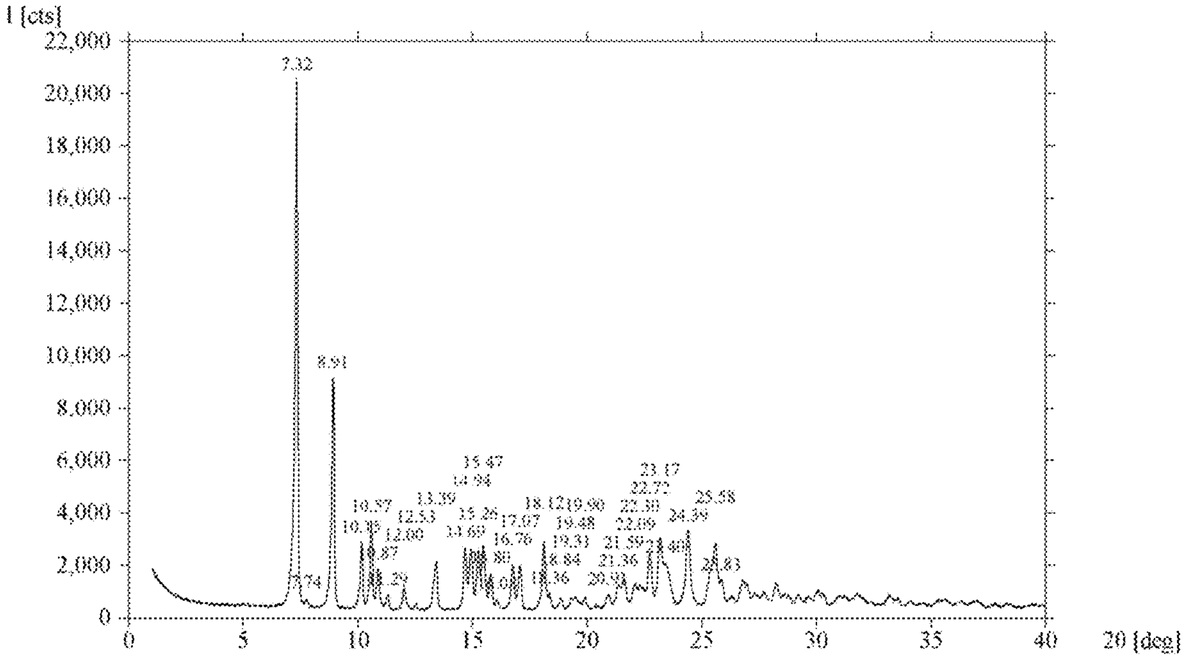
FIG. 1 is an x-ray powder diffraction (XRPD) pattern of the bis-HCl salt of compound of Structural Formula 1—Form A.

A description of example embodiments of the invention follows.

Crystalline Forms of Bis-HCl Salts of Compound of Structural Formula 1

Provided herein are crystalline forms of the bis-HCl salt of compound of Structural Formula 1, designated crystalline Form A, crystalline Form B, crystalline Form C and crystalline Form D.

"Crystalline," as used herein, refers to a homogeneous solid formed by a repeating, three-dimensional pattern of atoms, ions or molecules (e.g., an anhydrous molecule or a salt thereof, solvate thereof, or combination of the foregoing) having fixed distances between constituent parts. The unit cell is the simplest repeating unit in this pattern.

A crystalline form provided herein can be a single crystalline form or can comprise a mixture of two or more different crystalline forms. For example, in some embodiments, crystalline Forms A, B, C, and D of the bis-HCl salt of compound of Structural Formula 1 are provided as single crystalline forms (i.e., single crystalline Form A, single crystalline Form B, single crystalline Form C, single crystalline Form D). Alternatively, a crystalline form can comprise a mixture of two or more crystalline forms of compound of Structural Formula 1 (e.g., a mixture of two or more of crystalline Forms A, B, C, and D, specifically, of crystalline Forms C and D).

"Single crystalline form," as used herein, refers to a single crystal of a crystalline solid or a plurality of crystals of a crystalline solid wherein each of the plurality of crystals has the same crystal form.

The crystalline forms provided herein can be identified on the basis of characteristic peaks in an x-ray powder diffraction (XRPD) analysis. XRPD is a scientific technique that measures the x-rays, neutrons or electrons scattered by a powder or microcrystalline material as a function of scattering angle. XRPD can be used to identify and characterize crystalline solids, as the diffraction pattern produced by a particular solid is typically distinctive to that solid and can be used as a "fingerprint" to identify that solid. For example, an XRPD pattern or diffractogram (e.g., a pattern or diffractogram produced by a sample, such as an unknown sample) that is substantially in accordance with a reference XRPD pattern or diffractogram can be used to determine the identity between the sample material and the reference material. Both the position and the relative intensity of the peaks in an XRPD diffractogram are indicative of the particular phase and identity of a material.

FIGS. 1, 5, 9, and 13 show XRPD patterns of various crystalline forms described herein. An XRPD pattern that is "substantially in accordance" with one or more figures herein showing an XRPD pattern or diffractogram is an XRPD pattern that would be considered by one skilled in the art to represent the same crystalline form of the compound of Structural Formula 1 as the sample of the compound of Structural Formula 1 that provided the XRPD pattern of one or more figures provided herein. Thus, an XRPD pattern that is substantially in accordance may be identical to that of one of the figures or, more likely, may be somewhat different from one or more of the figures. An XRPD pattern that is somewhat different from one or more of the figures may not necessarily show each of the lines of the diffraction pattern presented herein and/or may show a slight change in appearance or intensity of the lines or a shift in the position of the lines. These differences typically result from differences in the conditions involved in obtaining the data or differences in the purity of the sample used to obtain the data. A person skilled in the art is capable of determining if a sample of a crystalline compound is of the same form as or a different form from a form disclosed herein by comparison of the XRPD pattern of the sample and the corresponding XRPD pattern disclosed herein.

It is to be understood that any 2θ angle specified herein means the specified value 0.2°. For example, when a described embodiment or a claim specifies a 2θ of 4.4°, this is to be understood to mean 4.4°±0.2°, that is, a 2θ angle of from 4.2° to 4.6°.

The crystalline forms provided herein can also be identified on the basis of differential scanning calorimetry (DSC) and/or thermogravimetric analysis (TGA). DSC is a thermoanalytical technique in which the difference in the amount of heat required to increase the temperature of a sample is measured as a function of temperature. DSC can be used to detect physical transformations, such as phase transitions, of a sample. For example, DSC can be used to detect the temperature(s) at which a sample undergoes crystallization, melting or glass transition.

TGA is a method of thermal gravimetric analysis in which changes in physical and chemical properties of a material are measured as a function of increasing temperature (with constant heating rate) or as a function of time (with constant temperature and/or constant mass loss). TGA can provide information about physical phenomena, such as second-order phase transitions, or about chemical phenomena, such as desolvation and/or decomposition.

FIGS. 3, 7, 11, and 15 show DSC thermograms of various crystalline forms described herein. FIGS. 2, 6, 10, and 14 show TGA thermograms of various crystalline forms described herein. A DSC or TGA thermogram that is "substantially in accordance" with one or more figures herein showing a DSC or TGA thermogram is a DSC or TGA thermogram that would be considered by one skilled in the art to represent the same crystalline form of the compound of Structural Formula 1 as the sample of the compound of Structural Formula 1 that provided the DSC or TGA thermogram of one or more figures provided herein.

It is to be understood that any temperature associated with DSC or TGA specified herein means the specified value ±5° C. or less. For example, when an embodiment or a claim specifies an endothermic peak at about 179° C., this is to be understood to mean 179° C.±5° C. or less, that is a temperature of from 174° C. to 184° C. In preferred embodiments, a DSC or TGA temperature is the specified value ±3° C., in more preferred embodiments, ±2° C.

The crystalline forms provided can be additionally characterized by dynamic vapor sorption (DVS), wherein a sample is subjected to varying conditions of humidity and temperature, and the response of the sample is measured gravimetrically. The result of a DVS analysis particularly can be a dual curve providing sample weight percent as a function of relative humidity (RH) over time, a dual curve providing sample water content as a function of RH over time, a curve providing weight percent in relation to RH, or a curve providing water content in relation to RH. Equipment useful for measuring such data is known in the art, and any such equipment can be used to measure the compounds according to the present invention. In certain embodiments, DVS analysis can be carried out by scanning at a series of specific RH values. Thus, specific polymorphs according to the invention may be identified and described in relation to the representative graph and/or the approximate peaks obtained in DVS analysis, particularly scanning from 0% to 95% RH with a step interval of 5% or 10% RH.

FIGS. 4, 8, 12, and 16 show DVS patterns of various crystalline forms described herein. A DVS pattern that is "substantially in accordance" with one or more figures herein showing a DVS patterns is a DVS pattern that would be considered by one skilled in the art to represent the same crystalline form of the compound of Structural Formula 1 as the sample of the compound of Structural Formula 1 that provided the DVS pattern of one or more figures provided herein.

In some embodiments, crystalline forms are solvates. "Solvate," as used herein, refers to a chemical compound formed by the interaction of a solute (e.g., a compound of Structural Formula 1) and one or more solvents (e.g., methanol, ethanol, water). Thus, "solvate" includes solvates containing a single type of solvent molecule and solvates containing more than one type of solvent molecule (mixed solvates or co-solvates). Typically, the one or more solvents in solvates described herein is an organic solvent or a combination of organic solvents, although water can also form solvates, called hydrates.

Form A:

In a first embodiment, a crystalline form of a compound represented by the bis-HCl salt of compound of Structural Formula 1 is provided, wherein the crystalline form is Form A, and is characterized by at least three x-ray powder diffraction peaks at 2θ angles selected from 7.32°, 8.91°, 10.15°, and 10.57°, or at least four x-ray powder diffraction peaks at 2θ angles selected from 7.32°, 8.91°, 10.15°, 10.57°, 15.47°, and 24.39°, at least five x-ray powder diffraction peaks at 2θ angles selected from 7.32°, 8.91°, 10.15°, 10.57°, 15.47°, 18.12°, 23.17°, 24.39°, and 25.58°. In a particular embodiment, Form A is characterized by x-ray powder diffraction peaks at 2θ angles of 7.32°, 8.91°, 10.15°, and 10.57°, or by x-ray powder diffraction peaks at 2θ angles of 7.32°, 8.91°, 10.15°, 10.57°, 15.47°, and 24.39°, or by x-ray powder diffraction peaks at 2θ angles of 7.32°, 8.91°, 10.15°, 10.57°, 15.47°, 18.12°, 23.17°, 24.39°, and 25.58° or by x-ray powder diffraction peaks at 2θ angles of 7.32°, 8.91°, 10.15°, 10.57°, 14.69°, 14.94°, 15.26°, 15.47°, 18.12°, 23.17°, 24.39°, and 25.28°. In some embodiments, crystalline Form A is characterized by an x-ray powder diffraction pattern substantially in accordance with that depicted in FIG. 1.

Crystalline Form A may be further characterized by a differential scanning calorimetry thermogram comprising a broad, strong endothermic peak at about 76° C. or a strong exothermic peak at about 235° C., consistent with decomposition. In some embodiments, the TGA thermogram and/or the DSC thermogram are substantially in accordance with those in FIG. 2 or FIG. 3.

Crystalline Form A can be additionally characterized by dynamic vapor sorption pattern comprising a weight gain of about 19% at 75% RH and about 40% weight gain at 95% RH. In some embodiments the DVS pattern is substantially in accordance with the one found in FIG. 4.

In a particular embodiment, Form A is in the form of a solvate, for example, an ethanol solvate.

Form B:

In a second embodiment, a crystalline form of a compound represented by bis-HCl salt of compound of Structural Formula 1 is provided, wherein the crystalline form is Form B, and is characterized by at least three x-ray powder diffraction peaks at 2θ angles selected from 5.72°, 10.73°, 12.34°, and 16.89°, at least four x-ray powder diffraction peaks at 20 angles selected from 5.72°, 10.73°, 12.34°, 13.46°, 16.89°, and 21.57°, or at least five x-ray powder diffraction peaks at 2θ angles selected from 5.72°, 7.30°, 10.73°, 12.34°, 13.46°, 16.89°, 17.73°, 20.47°, and 21.57°.

In a particular embodiment, Form B is characterized by x-ray powder diffraction peaks at 2θ angles of 5.72°, 10.73°, 12.34°, and 16.89°, or by x-ray powder diffraction peaks at 2θ angles of 5.72°, 10.73°, 12.34°, 13.46°, 16.89°, and 21.57° or by x-ray powder diffraction peaks at 2θ angles of 5.72°, 7.30°, 10.73°, 12.34°, 13.46°, 16.89°, 17.73°, 20.47°, and 21.57°. In another particular embodiment, Form B is characterized by x-ray powder diffraction peaks at 2θ angles of 5.72°, 7.30°, 10.73°, 10.89°, 12.34°, 13.46°, 14.66°, 14.78°, 15.87°, 16.89°, 17.73°, 19.10°, 20.47°, 20.79°, 21.57°, 23.55°, and 24.93°. In some embodiments, crystalline Form B is characterized by an x-ray powder diffraction pattern substantially in accordance with that depicted in FIG. 5.

Crystalline Form B may be further characterized by a differential scanning calorimetry thermogram comprising a broad strong endothermic peak at 69° C., a weak endothermic peak at 230° C., and a strong exothermic peak at 236° C., consistent with decomposition. In some embodiments, the TGA thermogram and/or the DSC thermogram are substantially in accordance with those in FIG. 6 or FIG. 7.

Crystalline Form B can be additionally characterized by dynamic vapor sorption pattern comprising a weight gain of about 19% at 75% RH and about 40% weight gain at 95% RH. In some embodiments the DVS pattern is substantially in accordance with the one found in FIG. 8.

In an example embodiment, Form B can be a solvate.

Form C:

In a third embodiment, a crystalline form of a compound represented by the bis-HCl salt of compound of Structural Formula 1 is provided, wherein the crystalline form is Form C, and is characterized by at least three x-ray powder diffraction peaks at 2θ angles selected from 6.02°, 11.14°, 12.95°, and 18.57°, at least four x-ray powder diffraction peaks at 20 angles selected from 6.02°, 11.14°, 11.44°, 12.95°, and 18.57°, or at least five x-ray powder diffraction peaks at 2θ angles selected from 6.02°, 7.62°, 11.14°, 11.44°, 12.95°, 18.57°, 19.76°, 21.55°, 22.40°, and 26.55°. In a particular embodiment, Form C is characterized by x-ray powder diffraction peaks at 2θ angles of 6.02°, 11.14°, 12.95°, and 18.57°, or by x-ray powder diffraction peaks at 2θ angles of 6.02°, 7.62°, 11.14°, 11.44°, 12.95°, 18.57°, 19.76°, 21.55°, 22.40°, and 26.55°, or by x-ray powder diffraction peaks at 2θ angles of 6.02°, 7.62°, 11.14°, 11.44°, 12.95°, 14.05°, 15.31°, 16.67°, 18.57°, 19.76°, 21.55°, 22.40°, 26.13°, 26.55°, 28.19°. In some embodiments, crystalline Form C is characterized by an x-ray powder diffraction pattern substantially in accordance with that depicted in FIG. 9.

Crystalline Form C may be further characterized by a differential scanning calorimetry thermogram comprising abroad weak endothermic peak at 69° C., a weak endothermic peak at 79° C., and a strong exothermic peak at 240° C., consistent with decomposition. In some embodiments, the TGA thermogram and/or the DSC thermogram are substantially in accordance with those in FIG. 10 or FIG. 11.

Crystalline Form C can be additionally characterized by dynamic vapor sorption pattern comprising a weight gain of about 6.1% in the range of 35-45% RH, with a total weight gain of 25.3% between 5 and 95% RH. In some embodiments the DVS pattern is substantially in accordance with the one found in FIG. 12.

In a particular embodiment, Form C is in the form of a solvate, for example, a hydrate.

Form D:

In a fourth embodiment, a crystalline form of a compound represented by the bis-HCl salt compound of Structural Formula 1 is provided, wherein the crystalline form is Form D, and is characterized by at least three x-ray powder diffraction peaks at 2θ angles selected from 3.68°, 13.26°, 16.11°, and 16.97°, by at least four x-ray powder diffraction peaks at 20 angles selected from 3.68°, 9.78°, 13.26°, 16.11°, and 16.97°, or by at least five x-ray powder diffraction peaks at 2θ angles selected from 3.68°, 9.78°, 13.26°, 14.76°, 16.11°, 16.97°, 25.94°, and 26.62°. In a particular embodiment, Form D is characterized by x-ray powder diffraction peaks at 2θ angles of 3.68°, 13.26°, 16.11, and 16.97°, or by x-ray powder diffraction peaks at 2θ angles of 3.68°, 9.78°, 13.26°, 16.11°, and 16.97°, or by x-ray powder diffraction peaks at 2θ angles of 3.68°, 9.78°, 13.26°, 14.76°, 16.110, 16.97°, 25.94°, and 26.62°, or by x-ray powder diffraction peaks at 2θ angles of 3.68°, 6.39°, 9.78°, 13.26°, 14.26°, 14.76°, 16.11°, 16.97°, 20.65°, 25.94°, and 26.62°. In some embodiments, crystalline Form D is characterized by an x-ray powder diffraction pattern substantially in accordance with that depicted in any of FIG. 13.

Crystalline Form D may be further characterized by a differential scanning calorimetry thermogram comprising abroad weak endothermic peak at 69° C., a weak endothermic peak at 96° C., and a strong exothermic peak at 243° C., consistent with decomposition. In some embodiments, the TGA thermogram and/or the DSC thermogram are substantially in accordance with those in FIG. 14 or FIG. 15.

Crystalline Form D can be additionally characterized by dynamic vapor sorption pattern comprising a weight gain of about 2.7% in the range of 5-25% RH, followed by a rapid weight gain of about 10% in the range of 25-35% RH, followed by a low weight gain of about 3.7% in the range of 35-75% RH, with a total weight gain of about 39.2% between 5 and 95% RH. In some embodiments the DVS pattern is substantially in accordance with the one found in FIG. 16.

In a particular embodiment, Form D is in the form of a solvate, for example, a hydrate.

Compositions and Pharmaceutical Compositions

In another embodiment, the invention relates to a composition, comprising particles of one or more crystalline forms of a compound represented by the bis-HCl salt of Structural Formula 1:

(1)

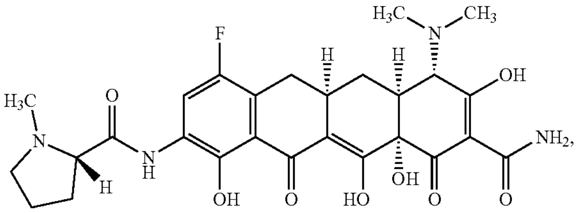

wherein, the one or more crystalline forms are selected from:

crystalline Form A characterized by x-ray powder diffraction peaks at 2θ angles selected from 7.32°, 8.91°, 10.15°, and 10.57°;

crystalline Form B characterized by x-ray powder diffraction peaks at 2θ angles selected from 5.72°, 10.73°, 12.34°, and 16.89°; crystalline Form C characterized by x-ray powder diffraction peaks at 2θ angles selected from 6.02°, 11.14°, 12.95°, and 18.57°; and crystalline Form D characterized by x-ray powder diffraction peaks at 2θ angles selected from 3.68°, 13.26°, 16.110, and 16.97°.

In another embodiment, the invention relates to a pharmaceutical composition, comprising particles of one or more crystalline forms of a compound represented by the bis-HCl salt of Structural Formula 1:

(1)

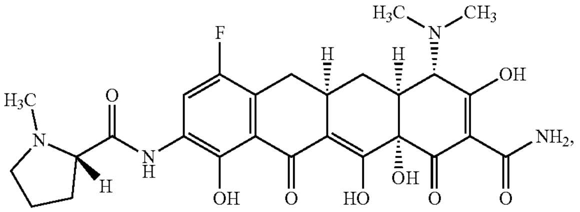

wherein, the one or more crystalline forms are selected from:

crystalline Form A characterized by x-ray powder diffraction peaks at 2θ angles selected from 7.32°, 8.91°, 10.15°, and 10.57°;

crystalline Form B characterized by x-ray powder diffraction peaks at 2θ angles selected from 5.72°, 10.73°, 12.34°, and 16.89°;

crystalline Form C characterized by x-ray powder diffraction peaks at 2θ angles selected from 6.02°, 11.14°, 12.95°, and 18.57°; and crystalline Form D characterized by x-ray powder diffraction peaks at 2θ angles selected from 3.68°, 13.26°, 16.110, and 16.97°, and a pharmaceutically acceptable carrier.

In certain embodiments, the invention relates to the compositions and pharmaceutical compositions as described herein, wherein the crystalline form is characterized by at least three x-ray powder diffraction peaks at 2θ angles selected from 3.68°, 9.78°, 13.26°, 16.110, and 16.97°, at least four x-ray powder diffraction peaks at 2θ angles selected from 3.68°, 9.78°, 13.26°, 16.110, and 16.97°, or at least five x-ray powder diffraction peaks at 2θ angles selected from 3.68°, 9.78°, 13.26°, 14.76°, 16.110, 16.97°, 25.94°, and 26.62°.

In certain embodiments, the invention relates to compositions and pharmaceutical compositions described herein, wherein the crystalline form is characterized by x-ray powder diffraction peaks at 2θ angles of 3.68°, 13.26°, 16.110, and 16.97°, by x-ray powder diffraction peaks at 2θ angles of 3.68°, 9.78°, 13.26°, 16.110, and 16.97°, or by x-ray powder diffraction peaks at 2θ angles of 3.68°, 9.78°, 13.26°, 14.76°, 16.11°, 16.97°, 25.94°, and 26.62°.

Figure 13:
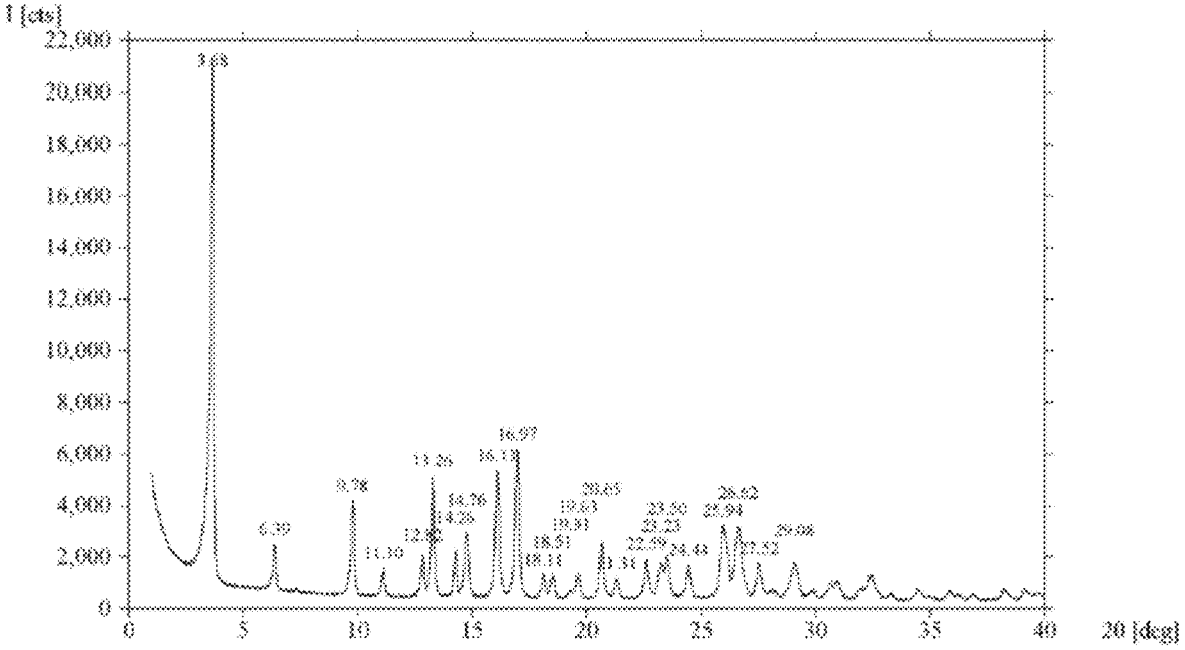
FIG. 13 is an XRPD pattern of the bis-HCl salt of compound of Structural Formula 1—Form D.

In certain embodiments, the invention relates to compositions and pharmaceutical compositions described herein, wherein the crystalline form is characterized by an x-ray powder diffraction pattern substantially in accordance with that depicted in FIG. 13.

The term "pharmaceutically acceptable carrier" means a non-toxic solvent, dispersant, excipient, adjuvant or other material which is mixed with the active ingredient in order to permit formation of a pharmaceutical composition, i.e., a dosage form capable of being administered to a subject. A "pharmaceutically acceptable carrier" should not destroy the activity of the compound with which it is formulated. Pharmaceutically acceptable carriers are well known in the art.

Pharmaceutically acceptable carriers, adjuvants or vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutical compositions of the invention may be administered orally, parenterally (including subcutaneous, intramuscular, intravenous and intradermal), by inhalation spray, topically, rectally, nasally, buccally, vaginally or via an implanted reservoir. In some embodiments, provided pharmaceutical compositions are administrable intravenously and/or intraperitoneally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the pharmaceutical compositions are administered orally, subcutaneously, intraperitoneally or intravenously. Sterile injectable forms of the pharmaceutical compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Specific pharmaceutically acceptable carriers suitable for use in an oral formulation such as a tablet or capsule include, but are not limited to, microcrystalline cellulose (Avicel PH101), croscarmellose Sodium (Ac-Di-Sol), kollidon 30 powder (polyvinylpyrrolidone, povidone), colloidal silicon dioxide M5-P, magnesium stearate, microcrystalline cellulose (Avcel PH102), sodium lauryl sulfate (Kolliphor SLS Fine) and Colloidal Silicon Dioxide M5-P. Each of the above listed carriers can be used in an oral formulation either alone or in any combination.

Further pharmaceutically acceptable carriers suitable for use in an oral formulation such as a tablet or capsule include, but are not limited to, microcrystalline cellulose (Avicel PHi 12), crospovidone (polyplasdone XL-10), colloidal silicone dioxide (Cab-O-Sil M-5P), Talc, starch and calcium stearate. In a particular aspect, the crystalline form (e.g., Form A, Form B, Form C, Form D or a mixture of Form C and Form D) is present in the oral formulation from about 25-45% by weight (freebase weight). In other aspects, Disodium EDTA is also present in the oral formulation. In certain aspects, the EDTA increases the bioavailability of the active. In a particular embodiment, the bioavailability of the active is increased by from about 1.5 fold to about 20 fold (e.g., 1.5, 2, 3, 4, 5, 6, 7, 8, 9, 10, 11, 12, 13, 14, 15, 16, 17, 18, 19 or 20 fold). When EDTA is present in the formulation, the w/w ratio of the crystalline form (freebase weight) to EDTA ranges from about 1:0.25 to about 1:15 (e.g., 1:0.25, 1:0.5, 1:1, 1:2.5, 1:5, 1:10, or 1:15). For ophthalmic use, provided pharmaceutical compositions may be formulated as micronized suspensions or in an ointment such as petrolatum.

Pharmaceutical compositions of this invention may also be administered by nasal aerosol or inhalation.

In some embodiments, pharmaceutical compositions of this invention are formulated for intra-peritoneal administration.

The amount of the crystalline form of a compound represented by the bis-HCl salt of compound of Structural Formula 1 in pharmaceutical compositions of this invention is such that is effective to measurably treat or prevent a tetracycline-responsive disease or disorder, in a biological sample or in a subject. In certain embodiments, a pharmaceutical composition of this invention is formulated for administration to a subject in need of such pharmaceutical composition. The term "subject," as used herein, means an animal. In some embodiments, the animal is a mammal. In certain embodiments, the subject is a veterinary patient (i.e., a non-human mammal patient, such as a dog, a cat, a horse, a pig or a rodent, such as a mouse or rat). In some embodiments, the subject is a dog. In other embodiments, the subject is a human (e.g., a human patient).

The amount of the crystalline form of a compound represented by the bis-HCl salt of compound of Structural Formula 1 that may be combined with the pharmaceutically acceptable carrier materials to produce a pharmaceutical composition in a single dosage form will vary depending upon the host treated and/or the particular mode of administration. In one embodiment, the pharmaceutical compositions should be formulated so that a dosage of between 0.01-100 mg/kg body weight/day of compound of Structural Formula 1 can be administered to a patient receiving these compositions. In another embodiment, the dosage is from about 0.5 to about 100 mg/kg of body weight, or between 1 mg and 1000 mg/dose, every 4 to 120 hours, or according to the requirements of the particular drug. Typically, the pharmaceutical compositions of this invention will be administered from about 1 to about 6 times per day. Exemplary doses, include but are not limited to, 1.0 mg/kg twice a day for about 4-14 days and 1.5 mg/kg once a day for 5 to 10 days.

It should also be understood that a specific dosage and treatment regimen for any particular subject (e.g., patient) will depend upon a variety of factors, including the activity of the specific compound of Structural Formula 1 employed, the age, body weight, general health, sex, diet, time of administration, rate of excretion, drug combination, and the judgment of the treating physician and the severity of the particular disease being treated.

Upon improvement of a subject's condition, a maintenance dose of a pharmaceutical composition of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Methods of Treatment and Uses for Pharmaceutical Compositions

In another embodiment, the invention relates to a method for treating or preventing a tetracycline-responsive disease or disorder, the method comprising administering to a subject in need thereof a therapeutically or prophylactically effective amount of one or more crystalline forms of a compound represented by the bis-HCl salt of Structural Formula 1:

(1)

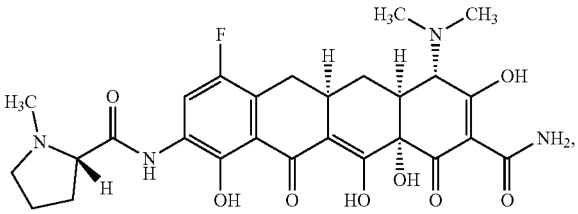

wherein, the one or more crystalline forms are selected from:

crystalline Form A characterized by x-ray powder diffraction peaks at 2θ angles selected from 7.32°, 8.91°, 10.15°, and 10.57°;

crystalline Form B characterized by x-ray powder diffraction peaks at 2θ angles selected from 5.72°, 10.73°, 12.34°, and 16.89°;

crystalline Form C characterized by x-ray powder diffraction peaks at 2θ angles selected from 6.02°, 11.14°, 12.95°, and 18.57°; and crystalline Form D characterized by x-ray powder diffraction peaks at 2θ angles selected from 3.68°, 13.26°, 16.110, and 16.97°, or a pharmaceutical composition comprising particles of Form A, Form B, Form C, Form D or mixtures thereof and a pharmaceutically acceptable carrier.

Pharmaceutical compositions described herein are generally useful for treatment or prevention of a tetracycline-responsive disease or disorder. Thus, in certain embodiments, the invention provides a method for treating a tetracycline-responsive disease or disorder, comprising administering to a subject in need thereof a therapeutically effective amount of a crystalline form, such as a crystalline form, of the bis-HCl salt of compound of Structural Formula 1, or a pharmaceutical composition described herein. The compound of Structural Formula 1 or crystalline form thereof, pharmaceutical composition thereof or combination of the foregoing can also be administered to cells in culture, e.g., in vitro or ex vivo, or to a subject, e.g., in vivo, to treat, prevent, and/or diagnose a variety of disorders, including those described herein.

The term "treat" or "treating" means to alleviate symptoms, eliminate the causation of the symptoms, either on a temporary or permanent basis, or to slow the appearance of symptoms of the named disorder or condition.

The term "therapeutically effective amount" means an amount of the bis-HCl salt of compound of Structural Formula 1 or crystalline form thereof (typically, in a pharmaceutical composition described herein) which is effective in treating or lessening the severity of one or more symptoms of a disorder or condition.

"Tetracycline-responsive disease or disorder" refers to a disease or disorder that can be treated, prevented, or otherwise ameliorated by the administration of a tetracycline compound of the present invention. Tetracycline-responsive disease or disorder includes infections, cancer, inflammatory disorders, autoimmune disease, arteriosclerosis, corneal ulceration, emphysema, arthritis, osteoporosis, osteoarthritis, multiple sclerosis, osteosarcoma, osteomyelitis, bronchiectasis, chronic pulmonary obstructive disease, skin and eye diseases, periodontitis, osteoporosis, rheumatoid arthritis, ulcerative colitis, prostatitis, tumor growth and invasion, metastasis, diabetes, diabetic proteinuria, panbronchiolitis; aortic or vascular aneurysms, skin tissue wounds, dry eye, bone, cartilage degradation, malaria, senescence, diabetes, vascular stroke, neurodegenerative disorders, cardiac disease, juvenile diabetes, acute and chronic bronchitis, sinusitis, and respiratory infections, including the common cold; Wegener's granulomatosis; neutrophilic dermatoses and other inflammatory diseases such as dermatitis herpetiformis, leukocytoclastic vasculitis, bullous lupus erythematosus, pustular psoriasis, erythema elevatum diutinum; vitiligo; discoid lupus erythematosus; pyoderma gangrenosum; pustular psoriasis; blepharitis, or meibomianitis; Alzheimer's disease; degenerative maculopathy; acute and chronic gastroenteritis and colitis; acute and chronic cystitis and urethritis; acute and chronic dermatitis; acute and chronic conjunctivitis; acute and chronic serositis; uremic pericarditis; acute and chronic cholecystis; cystic fibrosis, acute and chronic vaginitis; acute and chronic uveitis; drug reactions; insect bites; burns and sunburn, bone mass disorder, acute lung injury, chronic lung disorders, ischemia, stroke or ischemic stroke, skin wound, aortic or vascular aneurysm, diabetic retinopathy, hemorrhagic stroke, angiogenesis, and other states for which tetracycline compounds have been found to be active (see, for example, U.S. Pat. Nos. 5,789,395; 5,834,450; 6,277,061 and 5,532,227, each of which is expressly incorporated herein by reference).

In addition, the invention relates to methods of treating any disease or disease state that could benefit from modulating the expression and/or function of nitric oxide, metalloproteases, proinflammatory mediators and cytokines, reactive oxygen species, components of the immune response, including chemotaxis, lymphocyte transformation, delayed hypersensitivity, antibody production, phagocytosis, and oxidative metabolism of phagocytes. A method to treat any disease or disease state that could benefit from modulating the expression and/or function of C-reactive protein, signaling pathways (e.g., FAK signaling pathway), and/or augment the expression of COX-2 and PGE2 production is covered. A method to treat any disease or disease state that could benefit from inhibition of neovascularization is covered.

In certain embodiments, compositions of the invention can be used to prevent or treat important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., Cancer Res., 48: 6686-6690 (1988)).

Infections that can be treated using compositions of the invention include, but are not limited to, skin infections, GI infections, urinary tract infections (e.g., complication UTI), complicated intra-abdominal infections, genito-urinary infections, respiratory tract infections, sinuses infections, middle ear infections, systemic infections, cholera, influenza, bronchitis, acne, malaria, sexually transmitted disease including syphilis and gonorrhea, Legionnaires' disease, Lyme disease, Rocky Mountain spotted fever, Q fever, typhus, bubonic plague, gas gangrene, hospital acquired infections, leptospirosis, whooping cough, anthrax and infections caused by the agents responsible for lymphogranuloma venereum, inclusion conjunctivitis, or psittacosis. Infections can be bacterial, fungal, parasitic and viral infections (including those which are resistant to other tetracycline compounds).

In one embodiment, the infection can be caused by bacteria. In another embodiment, the infection is caused by Gram-positive bacteria. In a specific aspect of this embodiment, the infection is caused by a Gram-positive bacterium selected from *Staphylococcus* spp., *Streptococcus* spp., *Propionibacterium* spp., *Enterococcus* spp., *Bacillus* spp., *Corynebacterium* spp., *Nocardia* spp., *Clostridium* spp., *Actinobacteria* spp., and *Listeria* spp.

In another embodiment, the infection is caused by a Gram-negative bacterium. In one aspect of this embodiment, the infection is caused by a proteobacteria (e.g., Betaproteobacteria and Gammaproteobacteria), including *Escherichia coli, Salmonella, Shigella*, other Enterobacteriaceae, *Pseudomonas, Moraxella, Helicobacter, Stenotrophomonas, Bdellovibrio*, acetic acid bacteria, *Legionella* or alpha-proteobacteria such as *Wolbachia*. In another aspect, the infection is caused by a Gram-negative bacteria selected from cyanobacteria, spirochaetes, green sulfur or green non-sulfur bacteria. In a specific aspect of this embodiment, the infection is caused by a Gram-negative bacteria selected from Enterobactericeae (e.g., *E. coli, Klebsiella pneumonia* including those containing extended-spectrum .beta.-lactamases and/or carbapenemases), Bacteroidaceae (e.g., *Bacteroides fragilis*), Vibrionaceae (*Vibrio cholerae*), Pasteurellae (e.g., *Haemophilus* influenza), Pseudomonadaceae (e.g., *Pseudomonas aeruginosa*), Neisseriaceae (e.g. *Neisseria meningitidis*), Rickettsiae, Moraxellaceae (e.g., *Moraxella catarrhalis*), any species of Proteeae, *Acinetobacter* spp., *Helicobacter* spp., and *Campylobacter* spp.

In a particular embodiment, the infection is caused by Gram-negative bacterium selected from the group consisting of Enterobactericeae (e.g., *E. coli, Klebsiella pneumoniae*), *Pseudomonas*, and *Acinetobacter* spp.

In another embodiment, the infection is caused by an organism selected from the group consisting of *K. pneumoniae, Salmonella*, E. hirae, *A. baumanii, M. catarrhalis, H. influenzae, P. aeruginosa, E. faecium, E. coli, S. aureus*, and *E. faecalis*.

In another embodiment, the infection is caused by an organism selected from the group consisting of rickettsiae, chlamydiae, *Legionella* spp. and *Mycoplasma* spp.

In another embodiment, the infection is caused by an organism resistant to tetracycline or any member of first and second generation of tetracycline antibiotics (e.g., doxycycline or minocycline).

In another embodiment, the infection is caused by an organism resistant to methicillin.

In another embodiment, the infection is caused by an organism resistant to vancomycin.

In another embodiment, the infection is caused by an organism resistant to a quinolone or fluoroquinolone.

In another embodiment, the infection is caused by an organism resistant to tigecycline.

In another embodiment, the infection is caused by a multidrug-resistant pathogen (having intermediate or full resistance to any two or more antibiotics). In another embodiment the infection is a *Bacillus anthracis* infection. "*Bacillus anthracis* infection" includes any state, diseases, or disorders caused or which result from exposure or alleged exposure to *Bacillus anthracis* or another member of the *Bacillus cereus* group of bacteria. In another embodiment, the infection is caused by *Bacillus anthracis* (anthrax), *Yersinia pestis* (plague), or *Francisella tularensis* (tularemia).

In yet another embodiment, the infection can be caused by more than one organism described above. Examples of such infections include, but are not limited to, intra-abdominal infections (often a mixture of a gram-negative species like *E. coli* and an anaerobe like *B. fragilis*), diabetic foot (various combinations of *Streptococcus, Serratia, Staphylococcus* and *Enterococcus* spp., anaerobes (S. E. Dowd, et al., PloS one 2008; 3:e3326) and respiratory disease (especially in patients that have chronic infections like cystic fibrosis—e.g., *S. aureus* plus *P. aeruginosa* or H influenza, atypical pathogens), wounds and abscesses (various gram-negative and gram-positive bacteria, notably MSSA/MRSA, coagulase-negative staphylococci, enterococci, *Acinetobacter, P. aeruginosa, E. coli, B. fragilis*), and bloodstream infections (13% were polymicrobial (H. Wisplinghoff, et al., Clin. Infect. Dis. 2004; 39:311-317)).

In a further embodiment, the tetracycline responsive disease or disorder is not a bacterial infection. In another embodiment, the compositions of the invention are essentially non-antibacterial. For example, non-antibacterial compositions may have MIC values greater than about 4 μg/mL. In another embodiment, the compositions of the invention have both antibacterial and non-antibacterial effects.

Tetracycline responsive disease or disorder also includes diseases or disorders associated with inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, microorganisms, tissue necrosis, cancer or other agents. Acute inflammation is short-lasting, lasting only a few days. If it is longer lasting however, then it may be referred to as chronic inflammation.

IPASs include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders can be treated using the compounds of the invention or a pharmaceutically acceptable salt thereof include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; inflammatory bowel disorder; acute and chronic cystitis and urethritis; vasculitis; sepsis; nephritis; pancreatitis; hepatitis; lupus; inflammatory skin disorders including, for example, eczema, dermatitis, psoriasis, pyoderma gangrenosum, acne rosacea, and acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

IPASs also include matrix metalloproteinase associated states (MMPAS). MMPAS include states characterized by aberrant amounts of MMPs or MMP activity.

Examples of matrix metalloproteinase associated states ("MMPASs") can be treated using compositions of the invention include, but are not limited to, arteriosclerosis, corneal ulceration, emphysema, osteoarthritis, multiple sclerosis (Liedtke et al., Ann. Neurol. 1998, 44: 35-46; Chandler et al., J. Neuroimmunol. 1997, 72: 155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., Annu. Rev. Cell Biol. 1993, 9: 541-73; Tryggvason et al., Biochim. Biophys. Acta 1987, 907: 191-217; Li et al., Mol. Carcillog. 1998, 22: 84-89)), metastasis, acute lung injury, stroke, ischemia, diabetes, aortic or vascular aneurysms, skin tissue wounds, dry eye, bone and cartilage degradation (Greenwald et al., Bone 1998, 22: 33-38; Ryan et al., Curr. Op. Rheumatol. 1996, 8: 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In a further embodiment, the IPAS includes disorders described in U.S. Pat. Nos. 5,929,055; and 5,532,227, incorporated herein by reference in their entirety.

Tetracycline responsive disease or disorder also includes diseases or disorders associated with NO associated states. The term "NO associated states" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Examples of diseases or disorders associated with NO associated states can be treated using the compositions of the invention include, but are not limited to, malaria, senescence, diabetes, vascular stroke, neurodegenerative disorders (Alzheimer's disease and Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

In another embodiment, the tetracycline responsive disease or disorder is cancer. Examples of cancers that can be treated using the compounds of the invention or a pharmaceutically acceptable salt thereof include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostate carcinoma, lung cancer, and a variety of other cancers as well. The methods of the invention also cause the inhibition of cancer growth in adenocarcinomas, such as, for example, those of the prostate, breast, kidney, ovary, testes, and colon. In one embodiment, the cancers treated by methods of the invention include those described in U.S. Pat. Nos. 6,100,248; 5,843,925; 5,837,696; or 5,668,122, incorporated herein by reference in their entirety.

Alternatively, the compositions may be useful for preventing or reducing the likelihood of cancer recurrence, for example, to treat residual cancer following surgical resection or radiation therapy. The compositions useful according to the invention are especially advantageous as they are substantially non-toxic compared to other cancer treatments.

In a further embodiment, the compositions of the invention are administered in combination with standard cancer therapy, such as, but not limited to, chemotherapy.

Examples of tetracycline responsive states can be treated using the compositions of the invention or a pharmaceutically acceptable salt thereof also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoffs psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity.

Further neurological disorders include, for example, those listed in the American Psychiatric Association's Diagnostic and Statistical manual of Mental Disorders (DSM), the most current version of which is incorporated herein by reference in its entirety.

In another embodiment, the tetracycline responsive disease or disorder is diabetes. Diabetes that can be treated using the compositions of the invention include, but are not limited to, juvenile diabetes, diabetes mellitus, diabetes type I, or diabetes type II. In a further embodiment, protein glycosylation is not affected by the administration of the compositions of the invention. In another embodiment, the composition of the invention is administered in combination with standard diabetic therapies, such as, but not limited to insulin therapy.

In another embodiment, the tetracycline responsive disease or disorder is a bone mass disorder. Bone mass disorders that can be treated using the compounds of the invention or a pharmaceutically acceptable salt thereof include disorders where a subject's bones are disordered and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the compositions of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline responsive disease or disorder is acute lung injury. Acute lung injuries that can be treated using the compounds of the invention or a pharmaceutically acceptable salt thereof include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The tetracycline responsive disease or disorders of the invention also include chronic lung disorders. Examples of chronic lung disorders that can be treated using the compounds of the invention or a pharmaceutically acceptable salt thereof include, but are not limited, to asthma, cystic fibrosis, chronic obstructive pulmonary disease (COPD), and emphysema. In a further embodiment, the acute and/or chronic lung disorders that can be treated using the compositions of the invention include those described in U.S. Pat. Nos. 5,977,091; 6,043,231; 5,523,297; and 5,773,430, each of which is hereby incorporated herein by reference in its entirety.

In yet another embodiment, the tetracycline responsive disease or disorder is ischemia, stroke, or ischemic stroke.

In a further embodiment, the compositions of the invention can be used to treat such disorders as described above and in U.S. Pat. Nos. 6,231,894; 5,773,430; 5,919,775 and 5,789,395, incorporated herein by reference.

In another embodiment, the tetracycline responsive disease or disorder is a skin wound. The invention also provides a method for improving the healing response of the epithelialized tissue (e.g., skin, mucosae) to acute traumatic injury (e.g., cut, burn, scrape, etc.). The method includes using a composition of the invention to improve the capacity of the epithelialized tissue to heal acute wounds. The method may increase the rate of collagen accumulation of the healing tissue. The method may also decrease the proteolytic activity in the epithelialized tissue by decreasing the collagenolytic and/or gellatinolytic activity of MMPs. In a further embodiment, the tetracycline compound of the invention or a pharmaceutically acceptable salt thereof is administered to the surface of the skin (e.g., topically). In a further embodiment, the compositions of the invention are used to treat a skin wound, and other such disorders as described in, for example, U.S. Pat. Nos. 5,827,840; 4,704,383; 4,935,412; 5,258,371; 5,308,839, 5,459,135; 5,532,227; and 6,015,804; each of which is incorporated herein by reference in its entirety.

In yet another embodiment, the tetracycline responsive disease or disorder is an aortic or vascular aneurysm in vascular tissue of a subject (e.g., a subject having or at risk of having an aortic or vascular aneurysm, etc.). The compositions may be effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the compositions of the invention are used to treat disorders described in U.S. Pat. Nos. 6,043,225 and 5,834,449, incorporated herein by reference in their entirety.

In still another embodiment, the compounds, compositions and pharmaceutical compositions of the invention can be used to treat oral mucositis. In a particular aspect, the oral mucositis is a result of chemotherapy, radiation or both. In another particular aspect, the subject having oral mucositis is undergoing chemotherapy and/or radiation therapy for head and neck cancer. In a specific aspect, the head and neck cancer is selected from: laryngeal cancer; hypopharyngeal cancer; nasal cavity cancer; paranasal sinus cancer; nasopharyngeal cancer; oral cancer; oropharyngeal cancer; and salivary gland cancer.

Combination Therapies

In some embodiments, a crystalline form of a compound represented by the bis-HCl salt of compound of Structural Formula 1 (e.g., Form A, B, C or D) is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, the compound of Structural Formula 1 may be administered with another therapeutic agent simultaneously or sequentially in separate unit dosage forms or together in a unit dosage form. Accordingly, the invention provides a unit dosage form comprising a crystalline form of the bis-HCl salt of compound of Structural Formula 1 (e.g., Form A, B, C or D), an additional therapeutic agent, and a pharmaceutically acceptable carrier.

In one embodiment, where a second therapeutic agent is administered to a subject, the effective amount of the crystalline form of a compound represented by the bis-HCl salt of compound of Structural Formula 1 is less than its effective amount would be where the second therapeutic agent is not administered. In another embodiment, the effective amount of the second therapeutic agent is less than its effective amount would be were the crystalline form of a compound represented by the bis-HCl salt of compound of Structural Formula 1 not administered. In this way, undesired side effects associated with high doses of either agent may be minimized. Other potential advantages (including without limitation improved dosing regimens and/or reduced drug cost) will be apparent to those of skill in the art.

Synthetic Methods

Also provided herein are synthetic methods for preparing crystalline forms of a compound represented by the bis-HCl salt of compound Structural Formula 1. In some aspects, a mixture of crystalline forms is produced. For example, the mixture may comprise two or more crystalline forms selected from Form A, Form B, Form C, or Form D.

Form A:

In one embodiment, the invention relates to a method of preparing a crystalline form of the bis-HCl salt of a compound represented by Structural Formula 1:

(1)

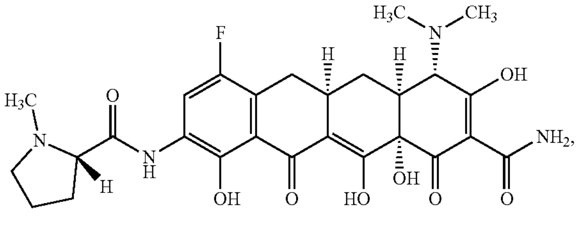

wherein the crystalline form is Form A and is characterized by at least three x-ray powder diffraction peaks at 2θ angles selected from 7.32°, 8.91°, 10.15°, and 10.57°, the method comprising:

(a) adding together amorphous bis-HCl salt of compound of Structural Formula 1 and a solvent mixture comprising ethanol, water, and concentrated HCl, thereby forming a recrystallization mixture of the amorphous compound;

(b) stirring for a sufficient time and at a sufficient temperature;

(c) filtering the resulting solution;

(d) adding crystalline particles of Form A (seed), stirring for a sufficient time and at a sufficient temperature;

(e) cooling the recrystallization mixture to a sufficient temperature and stirring for a sufficient time; and (f) isolating the particles of crystalline Form A, thereby preparing a composition comprising particles of crystalline Form A of the bis-HCl salt of compound of Structural Formula 1. The seed crystals of Form A were prepared according to the procedure in Example 1, section 1a.

In certain aspects of the method of preparing Form A, the relative amounts by volume of ethanol, water, and concentrated HCl in the recrystallization mixture is from about 20 to about 40 (ethanol), from about 10 to about 20 (water), and from about 2 to about 0.2 (concentrated HCl), for example about 33 (ethanol)/about 17 (water)/about 1 (concentrated HCl).

In some embodiments of the method of preparing Form A, the amount of the seed of Form A added in step (d) is from about 0.10% to about 5% of the total amount of amorphous bis-HCl salt of compound of Structural Formula 1 dissolved in the recrystallization mixture in step (a), for example from about 0.5% to about 2%. In certain embodiments the amount of added seed is about 1%.

In certain embodiments the recrystallization mixture in step (d) is stirred at a temperature in the range from about 18° C. to about 23° C. for a period of time from about 0.1 to about 10 hours, preferably from about 1 hour to about 5 hours, more preferably for 2 hours.

In certain embodiments the recrystallization mixture in step (e) is cooled to a temperature in the range from about 10° C. to about −10° C., preferably to about 0° C., and stirred for a period of time from about 0.1 hours to about 5 hours, preferably from about 0.5 hours to about 3 hours, more preferably for 1 hour.

In another aspect of the method of preparing Form A, the particles are isolated by filtration.

In yet another aspect, the method of preparing Form A further comprises washing the particles of crystalline Form A, for example, with ethanol or the mixture of water and concentrated HCl.

Form B:

In certain embodiments, the invention relates to a method of preparing a crystalline form of the bis-HCl salt of a compound represented by Structural Formula 1:

(1)

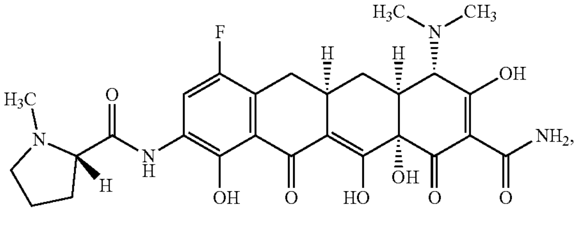

wherein the crystalline form is Form B and is characterized by at least three x-ray powder diffraction peaks at 2θ angles selected from 5.72°, 10.73°, 12.34°, and 16.89°, the method comprising:

(a) adding together the amorphous bis-HCl salt of compound of Structural Formula 1 and a solvent mixture comprising methanol and a solution of HCl in methanol, thereby forming a recrystallization mixture of the amorphous compound;

(b) adding isopropanol;

(c) stirring for a sufficient time and at a temperature in the range from about 18° C. to about 23° C.;

(d) isolating the particles of crystalline Form B, thereby preparing a composition comprising particles of crystalline Form B of the bis-HCl salt of compound of Structural Formula 1.

In some embodiments the concentration of the solution of HCl in methanol in step (a) is from about 3 mol/L to about 0.1 mol/L, preferably from about 2 mol/L to about 0.7 mol/L, more preferably about 1.25 mol/L.

In certain aspects of the method of preparing Form B, the ratio by volume of methanol/HCl solution in methanol in the recrystallization mixture is about 5/1, or about 3/1, or about 2/1, or about 1/2, or about 1/3, or about 1/5, preferably about 1.

In certain embodiments the ratio by volume of methanol and HCl solution in methanol mixture to isopropanol in step (b) is about 5/1, or about 3/1, or about 2/1, or about 1/2, or about 1/3, or about 1/5, preferably about 1.

In certain embodiments the recrystallization mixture in step (c) is stirred at a temperature in the range from about 18° C. to about 23° C. for a period of time from about 0.1 to about 2 hours, preferably from about 0.2 hours to about 1 hour, more preferably for 0.5 hours.

In another aspect of the method of preparing Form B, the particles are isolated by filtration.

In yet another aspect, the method of preparing Form B further comprises washing the particles of crystalline Form B, for example, with a mixture of isopropanol and methanol, with the ratio by volume of methanol and isopropanol of about 5/1, or about 3/1, or about 2/1, or about 1/2, or about 1/3, or about 1/5, preferably about 1.

In certain embodiments, the invention relates to a method of preparing a crystalline form of the bis-HCl salt of a compound represented by Structural Formula 1:

(1)

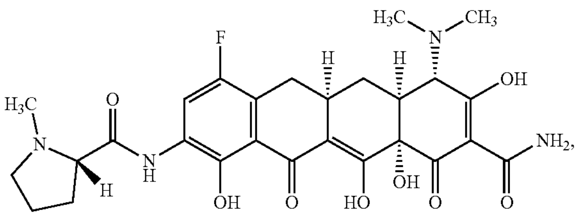

wherein the crystalline form is Form C and is characterized by at least three x-ray powder diffraction peaks at 2θ angles selected from 6.02°, 11.14°, 12.95°, and 18.57°, the method comprising:

(a) adding together the amorphous bis-HCl salt of compound of Structural Formula 1 and methanol, thereby forming a recrystallization mixture of the amorphous compound;
(b) filtering the recrystallization mixture;
(c) adding isopropanol;
(d) stirring for a sufficient time and at a temperature in the range from about 18° C. to about 23° C.;
(e) adding ethyl acetate;
(f) stirring for a sufficient time and at a sufficient temperature;
(g) isolating the particles of crystalline Form C, thereby preparing a composition comprising particles of crystalline Form C of the bis-HCl salt of compound of Structural Formula 1.

In certain embodiments the ratio by volume of methanol to isopropanol in step (c) is about 3/1, or about 2/1, or about or about 2/1, or about 1/2, or about 1/3, or about 1/5, preferably about 3/2.

In certain embodiments the recrystallization mixture in steps (d) and (f) is stirred at a temperature in the range from about 18° C. to about 23° C. for a period of time from about 0.1 to about 10 hours, preferably from about 1 hour to about 5 hours, more preferably for about 2 hours.

In certain embodiments the ratio by volume of ethyl acetate to the methanol and isopropanol mixture in step (e) is about 10, or about 5, or about 3, preferably about 4.5.

In some embodiments ethyl acetate is added to the recrystallization mixture over a period of time from about 0.1 to about 2 hours, preferably from about 0.5 to about 1.5 hours, more preferably over about 1 hour.

In another aspect of the method of preparing Form C, the particles are isolated by filtration.

In yet another aspect, the method of preparing Form C further comprises washing the particles of crystalline Form C, for example, with ethyl acetate.

In certain embodiments, the invention relates to a method of preparing a crystalline form of the bis-HCl salt of a compound represented by Structural Formula 1:

(1)

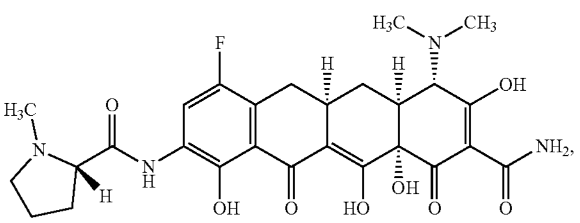

wherein the crystalline form is Form D and is characterized by at least three x-ray powder diffraction peaks at 2θ angles selected from 3.68°, 13.26°, 16.110, and 16.97°, the method comprising:

(a) suspending crystalline Form C of the bis-HCl salt of compound of Structural Formula 1 in a mixture of ethanol, water, and acetone, thereby forming a slurry of Form C;
(b) filtering the slurry of Form C thereby forming a recrystallization mixture;
(c) adding acetone, concentrated HCl, and crystalline particles (seeds) of Form D to the recrystallization mixture;
(d) stirring the mixture for a sufficient time and stirred at a temperature in the range from about 18° C. to about 23° C.;
(e) adding acetone to the mixture;
(f) stirring the mixture for a sufficient time and at a sufficient temperature; and
(c) isolating the solid particles of crystalline Form D, thereby preparing a composition comprising particles of crystalline Form D of the compound of Structural Formula 1. The seed crystals of form D were prepared according to the Example 4, section 4a.

In certain aspects of the method of preparing Form D, in step (a) the relative amounts by volume of methanol, water, and acetone in the slurry of Form C is from about 20 to about 5 (methanol), from about 10 to about 2 (acetone), and from about 2 to about 0.2 (water), preferably from about 15 to about 10 (methanol), from about 10 to about 5 (acetone), and from about 1.5 to about 0.5 (water), more preferably about 12 (methanol), about 6.7 (acetone), and about 1 (water).

In certain embodiments the ratio by volume of acetone to the combined volume of the recrystallization mixture in step (c) is about 2, or about 1, or about 0.1, preferably about 0.35.

In certain embodiments the ratio by volume of concentrated HCl to the combined volume of the recrystallization mixture in step (c) is about 0.2, or about 0.1, or about 0.05, preferably about 0.07.

In some embodiments of the method of preparing Form D, the amount of the seed of Form D added in step (d) is from about 0.02% to about 1% of the total amount of Form C suspended in step (a), for example from about 0.1% to about 0.5%, preferably about 0.2%.

In certain embodiments the recrystallization mixture in steps (d) is stirred at a temperature in the range from about 18° C. to about 23° C. for a period of time from about 10 to about 1 hours, preferably from about 7 hours to about 3 hours, more preferably for about 5 hours.

In certain embodiments the ratio by volume of acetone to the combined volume of the recrystallization mixture in step (e) is about 5, or about 3, or about 1, or about 0.5, preferably about 0.9.

In some embodiments acetone is added to the recrystallization mixture in step (e) over a period of time from about 0.1 to about 3 hours, preferably from about 0.5 to about 2 hours, more preferably over about 1.5 hours.

In certain embodiments the recrystallization mixture in step (f) is stirred at a temperature in the range from about 18° C. to about 23° C. for a period of time from about 6 to about 30 hours, preferably from about 12 hours to about 24 hours, more preferably for about 18 hours.

In yet another aspect, the method of preparing Form D further comprises washing the particles of crystalline Form D, for example, with a mixture of methanol and acetone, with the ratio by volume of methanol and acetone of about 2/1, or about 1, or about 1/2, or about 1/3, preferably about 1/5.

In certain embodiments, the invention relates to any of the methods described herein (methods to produce crystalline Forms A, B, C or D), further comprising step drying the isolated particles, for example at about 22° C. to about 30° C. for about 12 hours to about 5 days (e.g., from about 12 hours to about 24 hours) at about 26° C. for about 18 hours, or under nitrogen gas for about 1 hour to about 20 hours, then under vacuum conditions for about 15 hours to about 50 h, or under nitrogen gas for about 6 hour, then under vacuum conditions for about 48 h, or under nitrogen gas for about 10 h, then under vacuum conditions at about 25° C.

"Solvent system," as used herein, refers to a single solvent or a mixture of two or more (typically, two) different solvents. Exemplary solvents for a solvent system include water and organic solvents such as, but not limited to, methanol, ethanol, diisopropyl ether, isopropanol, ethyl acetate, and isopropyl acetate.

Isolating the solid particles of crystalline Form A, Form B, Form C, or Form D is typically effected by filtration and, optionally, rinsing of the filtered solids with a solvent (e.g., a chilled solvent), although other means of isolating the solid particles are known in the art. Other means of isolating the solid particles of crystalline Form A, Form B, Form C, or Form D include, but are not limited to, distilling liquid away from the solid particles or otherwise drying the solid particles, for example, by heating, by subjecting to reduced pressure (e.g., in vacuo) or any combination of the foregoing.

"Room temperature" and "ambient temperature," as used herein, means a temperature of from about 16° C. to about 25° C.

"Ambient conditions," as used herein, refers to room temperature and atmospheric pressure conditions.

Drying crystalline Form A, Form B, Form C, or Form D of the bis-HCl salt of the compound of Structural Formula 1 or a mixture comprising two or more crystalline forms of the bis-HCl salt of the compound of Structural Formula 1 can be accomplished, for example, by distilling any liquid present away from the solid crystalline form(s), by exposing the solid crystalline form(s) to ambient conditions or passing a stream of gas, such as nitrogen gas, over the solid crystalline form(s) (and thereby inducing the evaporation or desolvation of any liquid or entrapped volatile substance), by subjecting the solid crystalline form(s) to reduced pressure (e.g., in vacuo) or any combination of the foregoing.

It is understood that, quite often, in practice, the steps for preparing crystalline Form A, Form B, Form C, or Form D according to the methods described herein entail a combination of heating, maturing and/or drying.

EXEMPLIFICATION

General Materials and Methods

As used herein, compound of Structural Formula 1 is the compound represented by structural Formula 1.

XRPD

The data presented in this application contain x-ray diffraction patterns with labeled peaks and tables with peak lists. The range of data collected is instrument dependent. Under most circumstances, peaks within the range of up to about 30° 2Θ were selected. Rounding algorithms were used to round each peak to the nearest 0.1° or 0.01° 2Θ, depending upon the instrument used to collect the data and/or the inherent peak resolution. The location of the peaks along the x-axis (°2θ) in both the figures and the tables were determined using proprietary software and rounded to one or two significant figures after the decimal point based upon the above criteria. Peak position variabilities are given to within ±0.2° 2Θ based upon recommendations outlined in the USP discussion of variability in x-ray powder diffraction (United States Pharmacopeia, USP 38-NF 33 through S1, <941>Aug. 1, 2015). For d-space listings, the wavelength used to calculate d-spacings was 1.5405929 Å, the Cu-$K_{\alpha 1}$ wavelength (*Phys. Rev.* A56(6) 4554-4568 (1997)). Variability associated with d-spacing estimates was calculated from the USP recommendation, at each d-spacing, and provided in the respective tables.

Per USP guidelines, variable hydrates and solvates may display peak variances greater than 0.2° 2θ and therefore peak variances of 0.2° 2θ are not applicable to these materials.

"Prominent Peaks" are a subset of the entire observed peak list. Prominent peaks are selected from observed peaks by identifying preferably non-overlapping, low-angle peaks, with strong intensity.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks." In general, the more data collected to determine Representative Peaks, the more confident one can be of the classification of those peaks.

"Characteristic peaks," to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.2° 2θ. Not all crystalline polymorphs of a compound necessarily have at least one characteristic peak.

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-ray radiation through the specimen and onto the detector. Prior to the analysis, a silicon specimen (NIST SRM 640e) was analyzed to verify the observed position of the Si (111) peak is consistent with the NIST-certified position. A specimen of the sample was sandwiched between 3-μm-thick films and analyzed in transmission geometry. A beam-stop, short antiscatter extension, and antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

TGA

TG analyses for the crystalline Forms A and B described herein were performed using a TA Instruments TGA 500 thermogravimetric analyzer. Temperature calibration was performed using nickel. Each sample was placed in a platinum pan and inserted into the TG furnace. The furnace was heated under a nitrogen purge. The data acquisition parameters are displayed above each thermogram in the figures. The samples were heated from 25° C. to 300° C. at 10° C./min.

TG analyses for the crystalline Forms C and D described herein were performed using a Mettler Toledo TGA/DSC3+ analyzer. Balance check was performed using calcium oxalate, and temperature calibration was performed using indium, tin, and zinc. The sample was placed in an aluminum pan. The sample was sealed, the lid pierced, then inserted into the TG furnace. The furnace was heated under nitrogen.

DSC

DSC for the crystalline Forms A and B described herein was performed using a TA Instruments DSC 2000 differential scanning calorimeter. The furnace was heated under a nitrogen purge. The data acquisition parameters and pan configuration for each thermogram are displayed in the figures. The samples were heated from means 25° C. to 250-300° C. at 10° C./min.

DSC for the crystalline Forms C and D described herein was performed using a Mettler-Toledo DSC3+ differential scanning calorimeter. Temperature calibration was performed using octane, phenyl salicylate, indium, tin, and zinc. The samples were placed into aluminum DSC pans, covered with lids, and the weights were accurately recorded. A weighed aluminum pan configured as the sample pan was placed on the reference side of the cell. The pan lids were pierced prior to sample analysis.

DVS

DVS pattern for the crystalline Forms A and B was generated at 25° C. using a DVS Moisture Balance Flow System (Model Advantage) with the following conditions: sample size approximately 10 to 20 mg, drying at 25° C. for 60 minutes, adsorption range 0% to 95% RH, desorption range 95% to 0% RH, and step interval 5% RH. The equilibrium criterion was <0.01% weight change in 5 minutes for a maximum of 120 minutes.

DVS data for the crystalline Forms C and D were collected on a Surface Measurement System DVS Intrinsic instrument. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Example 1—Form A

1a. Preparation of Form A without Seed

Ethanol (4.8 mL), methanol (1.7 mL) and water (0.3 mL) were mixed. Concentrated HCl (0.15 mL) was added to the solvent mixture. The solvent mixture was cooled with an ice/water bath. Amorphous bis-HCl salt of compound of Structural Formula 1 (1 g) was added at below 20° C. The solution was allowed to stir at room temperature for 1 hour and then filtered through a 0.2 μm filter. The flask and filter were washed with 1.6 mL of ethanol and the washing was added to the crystallization solution. The solution was stirred at room temperature, then more ethanol (1.5 mL) and a small amount of amorphous bis-HCl salt of compound of Structural Formula 1 were added. All solids dissolved. The mixture was placed in a −20° C. freezer. After 45 min in the freezer needle-like crystals appeared. After the mixture was warmed up, the solids redissolved. The solution was placed in the freezer again, resulting in the formation of solids. After filtration at cold 404 mg of product as Form A was obtained. This product was used as seed in the further preparations of Form A.

1b. Preparation of Form A with Seed

The amorphous bis-HCl salt of compound of Structural Formula 1 (500 mg) was dissolved in a mixture of ethanol (2.5 mL), water (0.15 mL), and concentrated HCl (75 μL). The solution was polished filtered through a 0.2 μm PTFE filter. The container and the filter were washed with 1 mL of ethanol, and the washes were added to the recrystallization mixture. Seed crystals (5 mg) were added to the mixture. The mixture was allowed to stir at room temperature for 2 hours and then was cooled to 0° C., at which temperature the mixture was allowed to stir for another 1 hour. The mixture was filtered. The filter cake was washed twice with ethanol (0.5 mL and 0.25 mL) and then dried under nitrogen flush for 1 hour to give 400 mg of product as Form A.

The XRPD patterns of Form A is depicted in FIG. 1, and the peaks are tabulated in Table 1.

TABLE 1

| °2θ | d space (Å) | Intensity (%) |
|---|---|---|
| 7.32 ± 0.20 | 12.060 ± 0.329 | 100 |
| 7.74 ± 0.20 | 11.407 ± 0.294 | 4 |
| 8.91 ± 0.20 | 9.912 ± 0.222 | 45 |
| 10.15 ± 0.20 | 8.706 ± 0.171 | 14 |
| 10.57 ± 0.20 | 8.360 ± 0.158 | 18 |

TABLE 1-continued

| °2θ | d space (Å) | Intensity (%) |
|---|---|---|
| 10.87 ± 0.20 | 8.133 ± 0.149 | 9 |
| 11.29 ± 0.20 | 7.834 ± 0.138 | 4 |
| 12.00 ± 0.20 | 7.367 ± 0.122 | 6 |
| 12.53 ± 0.20 | 7.057 ± 0.112 | 3 |
| 13.39 ± 0.20 | 6.607 ± 0.098 | 11 |
| 14.69 ± 0.20 | 6.025 ± 0.082 | 13 |
| 14.94 ± 0.20 | 5.926 ± 0.079 | 13 |
| 15.26 ± 0.20 | 5.801 ± 0.076 | 13 |
| 15.47 ± 0.20 | 5.723 ± 0.074 | 14 |
| 15.80 ± 0.20 | 5.603 ± 0.070 | 8 |
| 16.08 ± 0.20 | 5.507 ± 0.068 | 4 |
| 16.76 ± 0.20 | 5.286 ± 0.063 | 10 |
| 17.07 ± 0.20 | 5.191 ± 0.060 | 10 |
| 18.12 ± 0.20 | 4.892 ± 0.054 | 14 |
| 18.36 ± 0.20 | 4.828 ± 0.052 | 5 |
| 18.84 ± 0.20 | 4.706 ± 0.050 | 3 |
| 19.31 ± 0.20 | 4.594 ± 0.047 | 4 |
| 19.48 ± 0.20 | 4.552 ± 0.046 | 4 |
| 19.90 ± 0.20 | 4.458 ± 0.044 | 4 |
| 20.91 ± 0.20 | 4.245 ± 0.040 | 4 |
| 21.36 ± 0.20 | 4.157 ± 0.038 | 6 |
| 21.59 ± 0.20 | 4.113 ± 0.038 | 7 |
| 22.09 ± 0.20 | 4.021 ± 0.036 | 6 |
| 22.30 ± 0.20 | 3.983 ± 0.035 | 6 |
| 22.72 ± 0.20 | 3.910 ± 0.034 | 12 |
| 23.17 ± 0.20 | 3.835 ± 0.033 | 15 |
| 23.40 ± 0.20 | 3.799 ± 0.032 | 10 |
| 24.39 ± 0.20 | 3.647 ± 0.029 | 16 |
| 25.58 ± 0.20 | 3.480 ± 0.027 | 14 |
| 25.83 ± 0.20 | 3.446 ± 0.026 | 7 |

Figure 2:
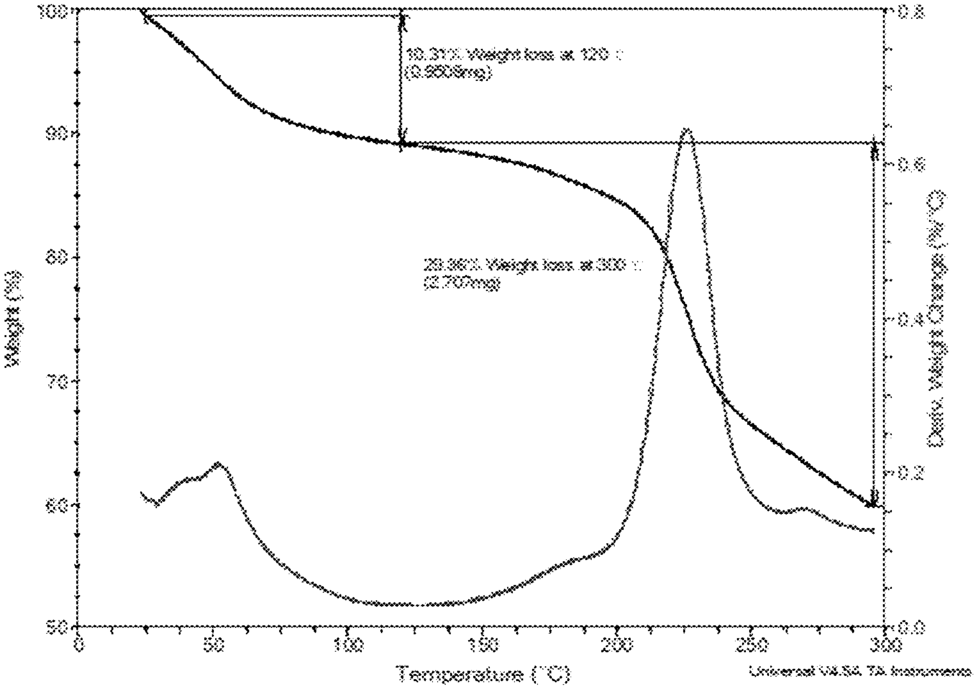
FIG. 2 is a thermogravimetric analysis (TGA) thermogram of the bis-HCl salt of compound of Structural Formula 1—Form A.

The TGA trace of Form A is depicted in FIG. 2. Weight losses of approximately 10.31% from ambient to 120° C., and about 19.05% from 125 to 295° C. were observed in the TG thermogram.

Figure 3:
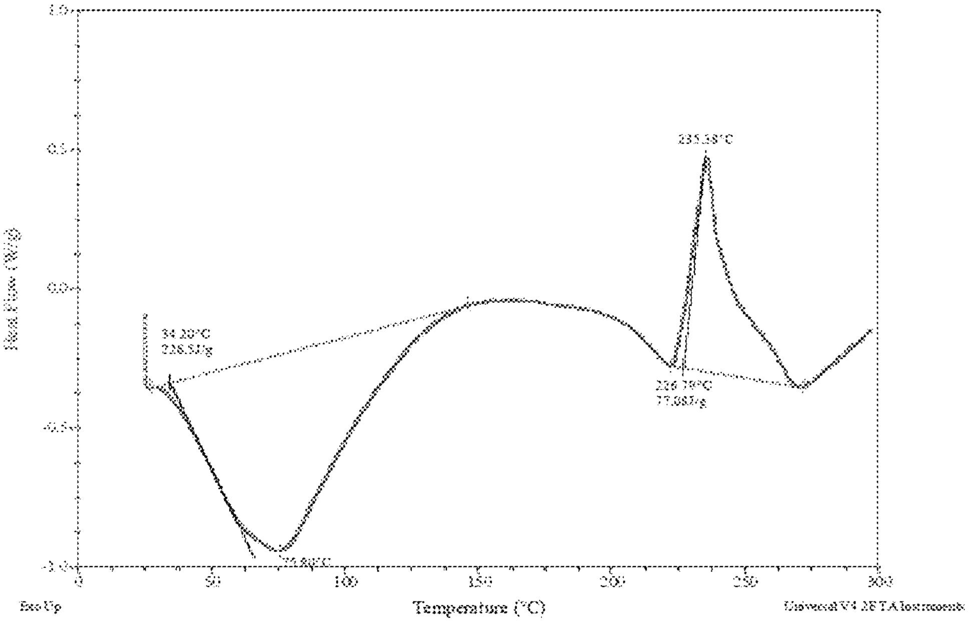
FIG. 3 is a differential scanning calorimetry (DSC) thermogram of the bis-HCl salt of compound of Structural Formula 1—Form A.

The DSC trace of Form A is depicted in FIG. 3. The DSC thermogram displays a broad endothermic peak at approximately 76° C. and an exothermic peak observed at approximately 235° C.

Figure 4:
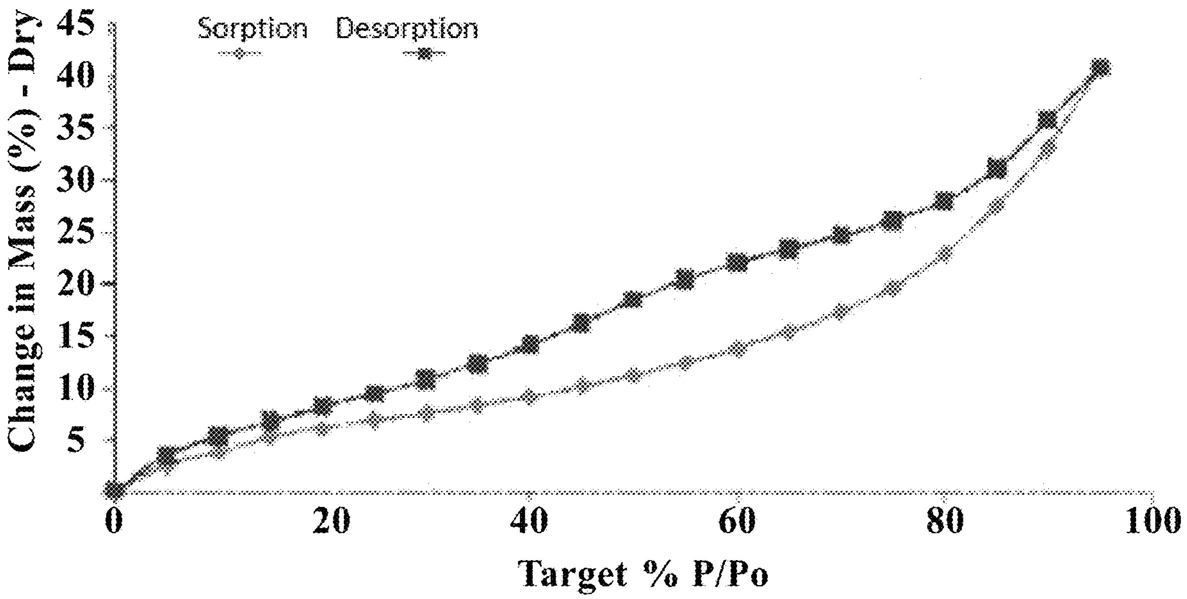
FIG. 4 is a dynamic vapor sorption (DVS) pattern of the bis-HCl salt of compound of Structural Formula 1—Form A.

The DVS pattern of Form A is depicted in FIG. 4. The DVS pattern displays a weight gain of about 19% at 75% RH and about 40% at 95% RH.

Example 2—Form B

Preparation of Form B

The amorphous bis-HCl salt of compound of Structural Formula 1 (1.42 g) was dissolved in a mixture of HCl/methanol (1.25 M, 2.85 mL) and methanol (2.85 mL). To the resulting solution was added isopropanol (2.85 mL). The mixture was allowed to stir and slowly became cloudy; solid appeared after 30 min of stirring. The mixture was filtered. The filter cake was washed with a mixture of methanol and isopropanol (1:1 v/v, 2.85 mL) and dried to give 0.58 g of product as Form B.

Figure 5:
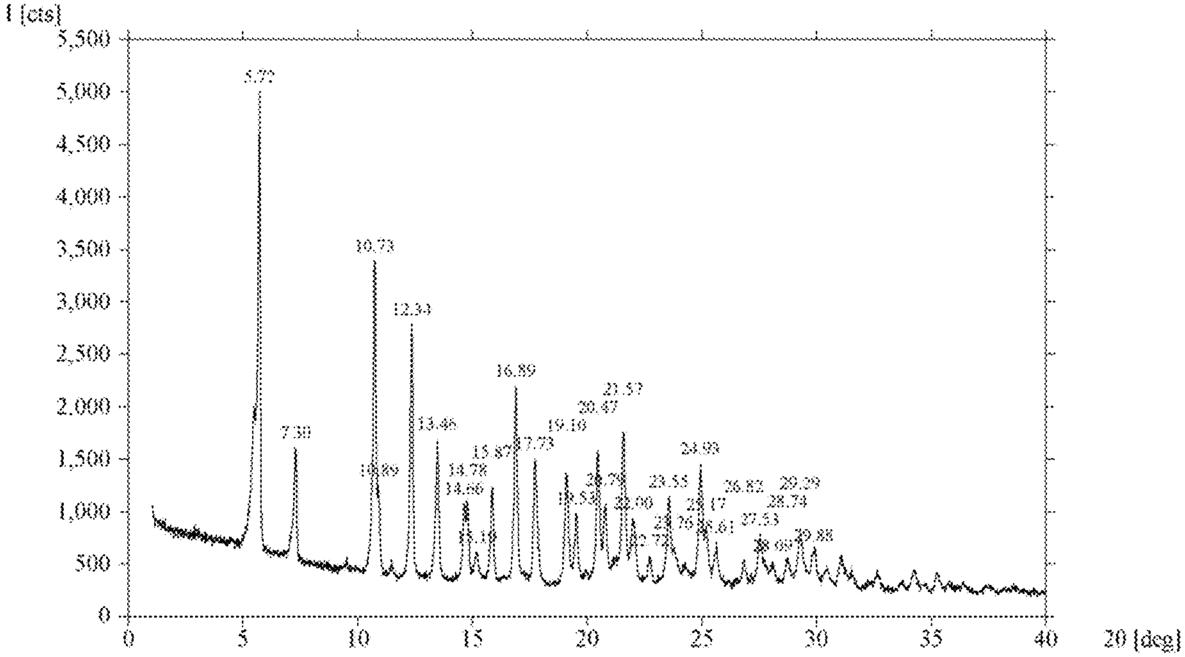
FIG. 5 is an XRPD pattern of the bis-HCl salt of compound of Structural Formula 1—Form B.

The XRPD pattern of Form B is depicted in FIG. 5 and the peaks are tabulated in Table 2.

TABLE 2

| °2θ | d space (Å) | Intensity (%) |
|---|---|---|
| 5.72 ± 0.20 | 15.437 ± 0.539 | 100 |
| 7.30 ± 0.20 | 12.097 ± 0.331 | 33 |
| 10.73 ± 0.20 | 8.238 ± 0.153 | 69 |
| 10.89 ± 0.20 | 8.116 ± 0.149 | 25 |
| 12.34 ± 0.20 | 7.170 ± 0.116 | 55 |
| 13.46 ± 0.20 | 6.574 ± 0.097 | 34 |
| 14.66 ± 0.20 | 6.039 ± 0.082 | 22 |
| 14.78 ± 0.20 | 5.987 ± 0.081 | 22 |

TABLE 2-continued

| °2θ | d space (Å) | Intensity (%) |
|---|---|---|
| 15.19 ± 0.20 | 5.827 ± 0.076 | 12 |
| 15.87 ± 0.20 | 5.581 ± 0.070 | 25 |
| 16.89 ± 0.20 | 5.244 ± 0.062 | 45 |
| 17.73 ± 0.20 | 4.998 ± 0.056 | 31 |
| 19.10 ± 0.20 | 4.642 ± 0.048 | 27 |
| 19.53 ± 0.20 | 4.543 ± 0.046 | 20 |
| 20.47 ± 0.20 | 4.335 ± 0.042 | 31 |
| 20.79 ± 0.20 | 4.270 ± 0.041 | 22 |
| 21.57 ± 0.20 | 4.116 ± 0.038 | 36 |
| 22.00 ± 0.20 | 4.037 ± 0.036 | 19 |
| 22.72 ± 0.20 | 3.911 ± 0.034 | 11 |
| 23.55 ± 0.20 | 3.775 ± 0.032 | 22 |
| 23.76 ± 0.20 | 3.741 ± 0.031 | 14 |
| 24.93 ± 0.20 | 3.569 ± 0.028 | 29 |
| 25.17 ± 0.20 | 3.535 ± 0.028 | 17 |
| 25.61 ± 0.20 | 3.475 ± 0.027 | 14 |
| 26.82 ± 0.20 | 3.321 ± 0.024 | 11 |
| 27.53 ± 0.20 | 3.237 ± 0.023 | 15 |
| 28.09 ± 0.20 | 3.174 ± 0.022 | 9 |
| 28.74 ± 0.20 | 3.104 ± 0.021 | 10 |
| 29.29 ± 0.20 | 3.047 ± 0.020 | 17 |
| 29.88 ± 0.20 | 2.988 ± 0.020 | 12 |

Figure 6:
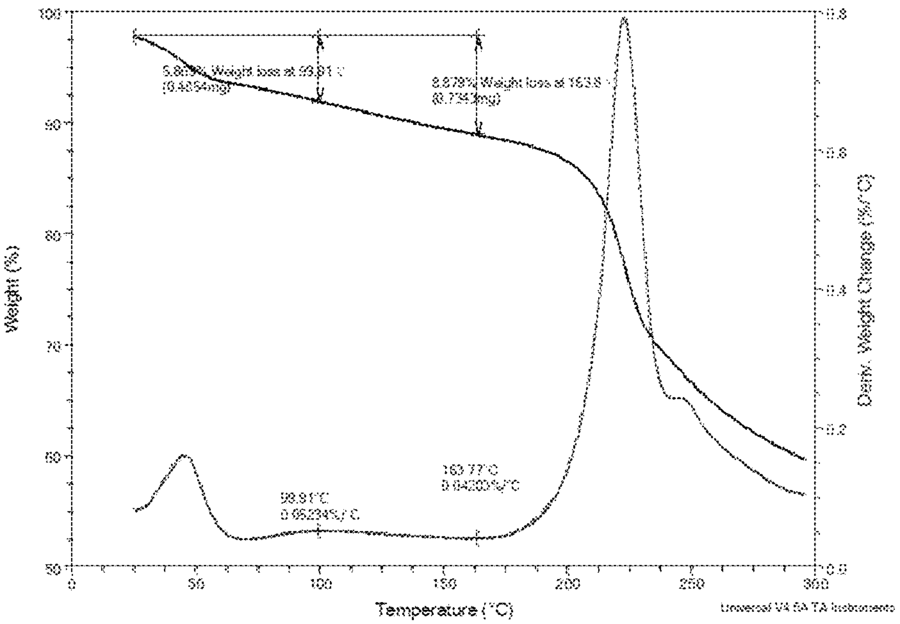
FIG. 6 is a TGA thermogram of the bis-HCl salt of compound of Structural Formula 1—Form B.

The TGA trace of Form B is depicted in FIG. 6. Weight losses of approximately 5.87% from ambient to 100° C. and 3.00% from 100 to 164° C. were observed in the TG thermogram.

Figure 7:
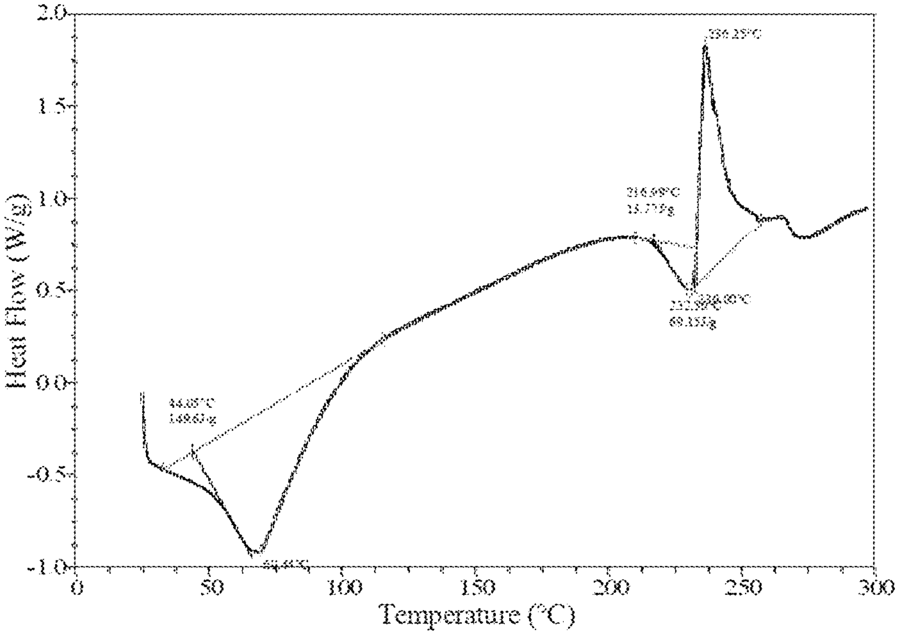
FIG. 7 is a DSC thermogram of the bis-HCl salt of compound of Structural Formula 1—Form B.
Figure 8:
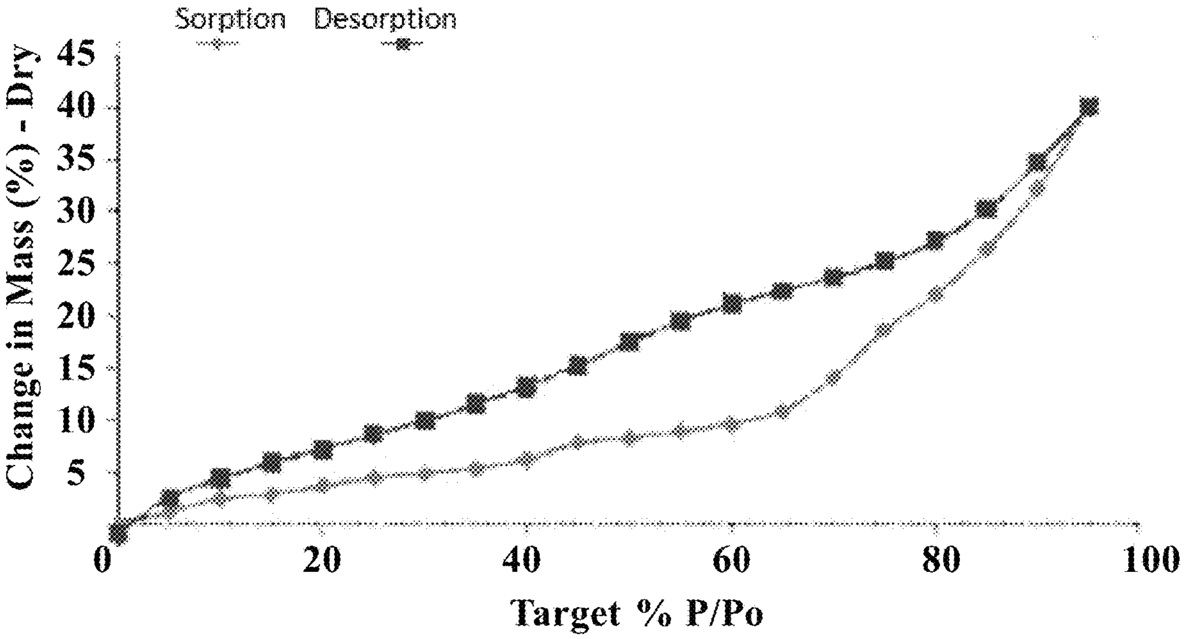
FIG. 8 is a DVS pattern of the bis-HCl salt of compound of Structural Formula 1—Form B.

The DSC trace of Form B is shown in FIG. 7. The DSC thermogram displays a broad strong endothermic peak at approximately 69° C., followed by a small endothermic peak at 230° C. and a large exothermic peak at 236° C.

The DVS pattern of Form A is depicted in FIG. 4. The DVS pattern displays a weight gain of about 19% at 75% RH and about 40% at 95% RH.

Example 3—Form C

Preparation of Form C

The amorphous bis-HCl salt of compound of Structural Formula 1 (498 g) was dissolved in 1.22 L of methanol. The solution was polished filtered. The container and filter were washed with 240 mL of methanol, and the washes were added to the recrystallization mixture. To the methanol solution was added 1.9 L of isopropanol in 15 min. The resulting mixture was allowed to stir at room temperature for 2 hours during which time a yellow suspension formed. Ethyl acetate (19 L) was added to the mixture over a period of 1 hour. The resulting mixture was allowed to stir for another 2 hours and then filtered. The filter cake was washed with ethyl acetate three times (2 L, 1 L, 1 L). The filter cake was dried on the filter funnel with nitrogen flow and vacuum for 16 hours and then in a vacuum oven for 3 days to give 357.5 g product as Form C.

Form C is a hexagonal unit cell, space group $P6_1$, with unit cell parameters:

a=16.923 Å b=16.923 Å c=18.870 Å unit cell volume=4680.4 $Å^3$

Figure 9:
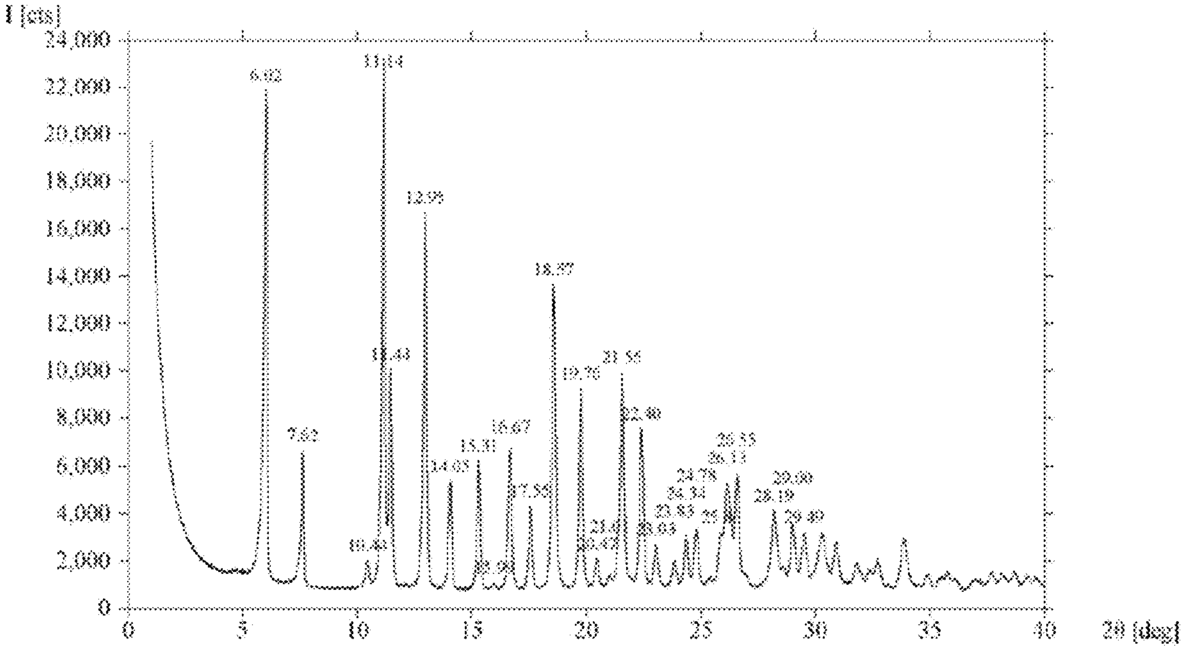
FIG. 9 is an XRPD pattern of the bis-HCl salt of compound of Structural Formula 1—Form C.

The XRPD pattern of Form C is depicted in FIG. 9 and the peaks are tabulated in Table 3.

TABLE 3

| °2θ | d space (Å) | Intensity (%) |
|---|---|---|
| 6.02 ± 0.20 | 14.678 ± 0.487 | 94 |
| 7.62 ± 0.20 | 11.596 ± 0.304 | 28 |
| 10.44 ± 0.20 | 8.466 ± 0.162 | 9 |
| 11.14 ± 0.20 | 7.939 ± 0.142 | 100 |
| 11.44 ± 0.20 | 7.726 ± 0.135 | 43 |
| 12.95 ± 0.20 | 6.832 ± 0.105 | 71 |
| 14.05 ± 0.20 | 6.300 ± 0.089 | 23 |
| 15.31 ± 0.20 | 5.783 ± 0.075 | 27 |
| 15.99 ± 0.20 | 5.540 ± 0.069 | 5 |
| 16.67 ± 0.20 | 5.314 ± 0.063 | 29 |
| 17.55 ± 0.20 | 5.048 ± 0.057 | 19 |
| 18.57 ± 0.20 | 4.774 ± 0.051 | 59 |
| 19.76 ± 0.20 | 4.490 ± 0.045 | 40 |
| 20.47 ± 0.20 | 4.336 ± 0.042 | 9 |
| 21.01 ± 0.20 | 4.225 ± 0.040 | 6 |
| 21.55 ± 0.20 | 4.120 ± 0.038 | 43 |
| 22.40 ± 0.20 | 3.966 ± 0.035 | 32 |
| 23.03 ± 0.20 | 3.858 ± 0.033 | 11 |
| 23.83 ± 0.20 | 3.730 ± 0.031 | 9 |
| 24.34 ± 0.20 | 3.653 ± 0.030 | 13 |
| 24.78 ± 0.20 | 3.590 ± 0.029 | 14 |
| 25.86 ± 0.20 | 3.443 ± 0.026 | 14 |
| 26.13 ± 0.20 | 3.408 ± 0.026 | 23 |
| 26.55 ± 0.20 | 3.354 ± 0.025 | 24 |
| 28.19 ± 0.20 | 3.163 ± 0.022 | 18 |
| 29.00 ± 0.20 | 3.076 ± 0.021 | 15 |
| 29.49 ± 0.20 | 3.027 ± 0.020 | 14 |

Figure 10:
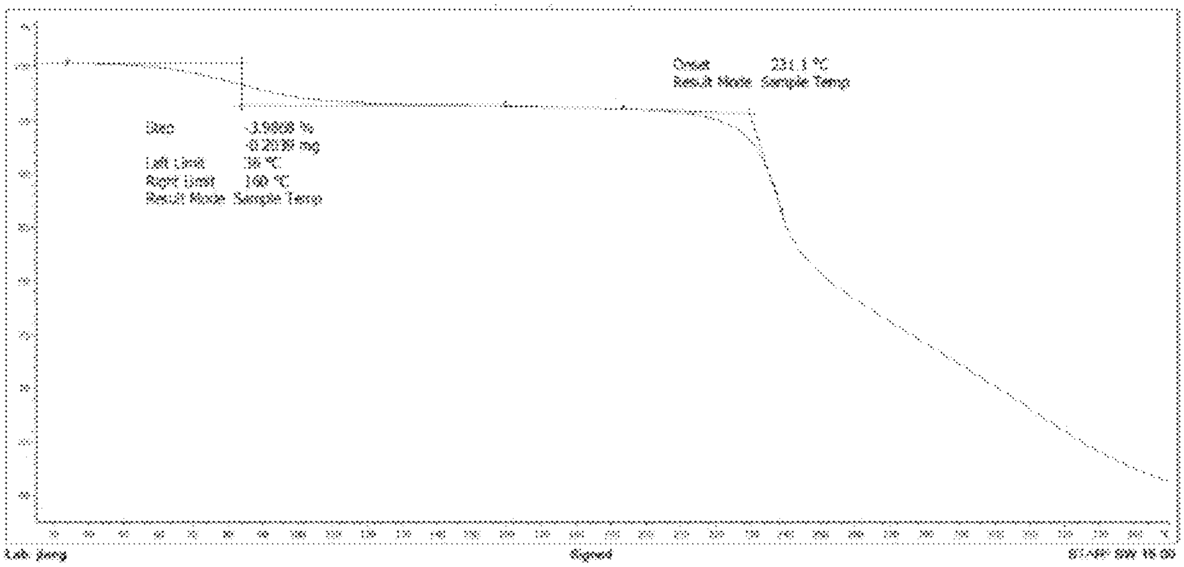
FIG. 10 is a TGA thermogram of the bis-HCl salt of compound of Structural Formula 1—Form C.

The TGA trace of Form C is depicted in FIG. 10.

Weight loss of approximately 4.0% was observed during heating from 36° C. to 160° C. in the TG thermogram.

Figure 11:
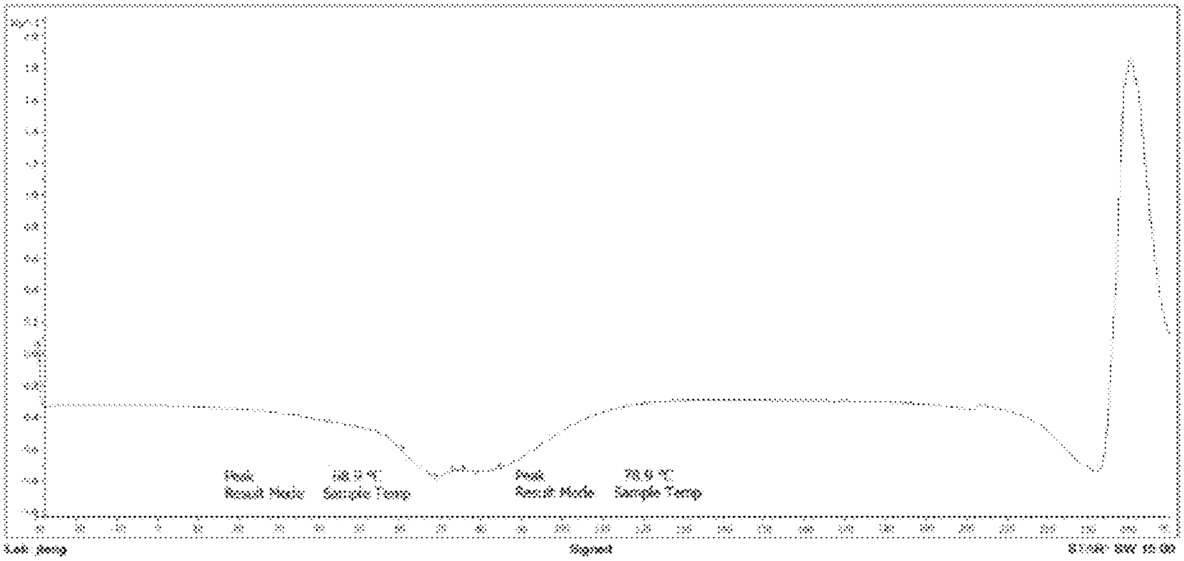
FIG. 11 is a DSC thermogram of the bis-HCl salt of compound of Structural Formula 1—Form C.

The DSC trace of Form C is shown in FIG. 11. The DSC thermogram displays a two overlapping broad endothermic peaks at approximately 69° C. and approximately 79° C., followed by large exothermic peak at about 240° C.

Figure 12:
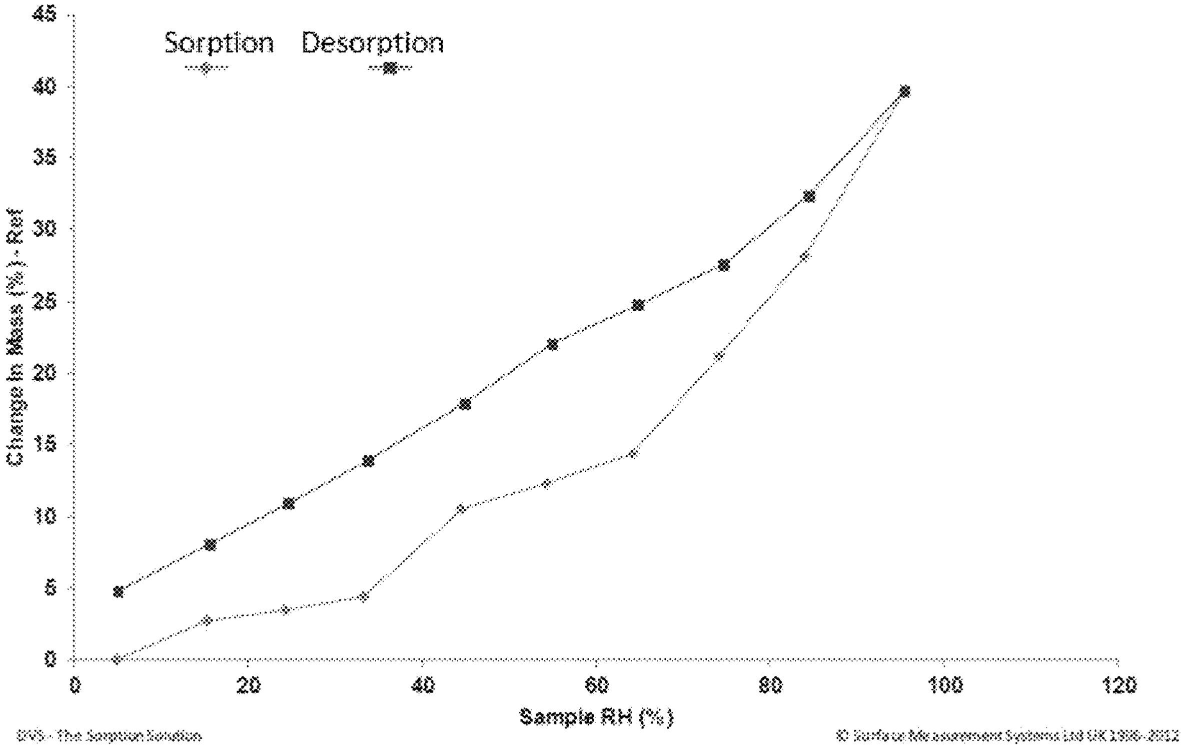
FIG. 12 is a DVS pattern of the bis-HCl salt of compound of Structural Formula 1—Form C.

The DVS pattern of Form C is depicted in FIG. 12 The DVS pattern displays a weight gain of about 6.1% in the range of 35-45% RH, with a total weight gain of 25.3% between 5 and 95% RH.

Example 4—Form D

4a. Preparation of Form D without Seed

Form C (0.5 g) was dissolved in methanol (2 ml) and water (0.15 mL). Acetone (3 mL) and concentrated HCl (0.2 mL) were added to the mixture. The mixture was allowed to stir at room temperature for 22 hours. Additional portion of acetone (2 mL) was added to the mixture, formation of solids was observed. The mixture was allowed to stir at room temperature for 18 hours and then filtered. The filter cake was dried to give 437 mg of the product as Form D. This product was used as seed in the further preparations of Form D.

4b. Preparation of Form D with Seed

Methanol (353.5 mL), acetone (202 mL) and water (30.3 mL) were mixed. Form C (101 g) was dissolved in 380 mL of the solvent mixture. The solution was polish filtered. The container and filter were washed with the remaining solvent mixture, and the washes were added to the solution of Form C. To the resulting mixture acetone (202 mL) and concentrated HCl (40.4 mL) were added, followed by Form D seed (200 mg). The mixture was allowed to stir at room temperature for 5 hours, during which time a thin suspension formed. Additional portion of acetone (760 mL) was slowly added to the mixture over a period of 1.5 hours. The mixture was allowed to stir at room temperature overnight and then filtered. The filter cake was washed with 250 mL of a mixture of methanol and acetone (1 to 5 by volume). The filter cake was dried on the funnel with vacuum and a nitrogen stream for 6 hours and then transferred into a glass bottle. The material was further dried in a vacuum oven at room temperature for 2 days to give 90.2 g product as Form D.

Form D is a hexagonal unit cell, space group $P3_1$, with unit cell parameters:

a=25.578 Å b=25.578 Å c=6.938 Å unit cell volume=4596.7 $Å^3$

The XRPD patterns of Form D is depicted in FIG. 13, and the peaks are tabulated in Table 4.

TABLE 4

| °2θ | d space (Å) | Intensity (%) |
|---|---|---|
| 3.68 ± 0.20 | 23.992 ± 1.304 | 100 |
| 6.39 ± 0.20 | 13.818 ± 0.432 | 12 |
| 9.78 ± 0.20 | 9.040 ± 0.184 | 20 |
| 11.10 ± 0.20 | 7.965 ± 0.143 | 7 |
| 12.82 ± 0.20 | 6.899 ± 0.107 | 10 |
| 13.26 ± 0.20 | 6.670 ± 0.100 | 24 |
| 14.26 ± 0.20 | 6.205 ± 0.087 | 11 |
| 14.76 ± 0.20 | 5.996 ± 0.081 | 14 |
| 16.11 ± 0.20 | 5.497 ± 0.068 | 26 |
| 16.97 ± 0.20 | 5.220 ± 0.061 | 29 |
| 18.11 ± 0.20 | 4.895 ± 0.054 | 6 |
| 18.51 ± 0.20 | 4.790 ± 0.051 | 6 |
| 19.31 ± 0.20 | 4.592 ± 0.047 | 3 |
| 19.63 ± 0.20 | 4.519 ± 0.046 | 6 |
| 20.65 ± 0.20 | 4.298 ± 0.041 | 12 |
| 21.31 ± 0.20 | 4.167 ± 0.039 | 6 |
| 22.59 ± 0.20 | 3.933 ± 0.034 | 9 |
| 23.23 ± 0.20 | 3.826 ± 0.032 | 8 |
| 23.50 ± 0.20 | 3.783 ± 0.032 | 10 |
| 24.44 ± 0.20 | 3.640 ± 0.029 | 8 |
| 25.94 ± 0.20 | 3.432 ± 0.026 | 15 |
| 26.62 ± 0.20 | 3.346 ± 0.025 | 15 |
| 27.52 ± 0.20 | 3.238 ± 0.023 | 8 |
| 29.08 ± 0.20 | 3.068 ± 0.021 | 8 |

Figure 14:
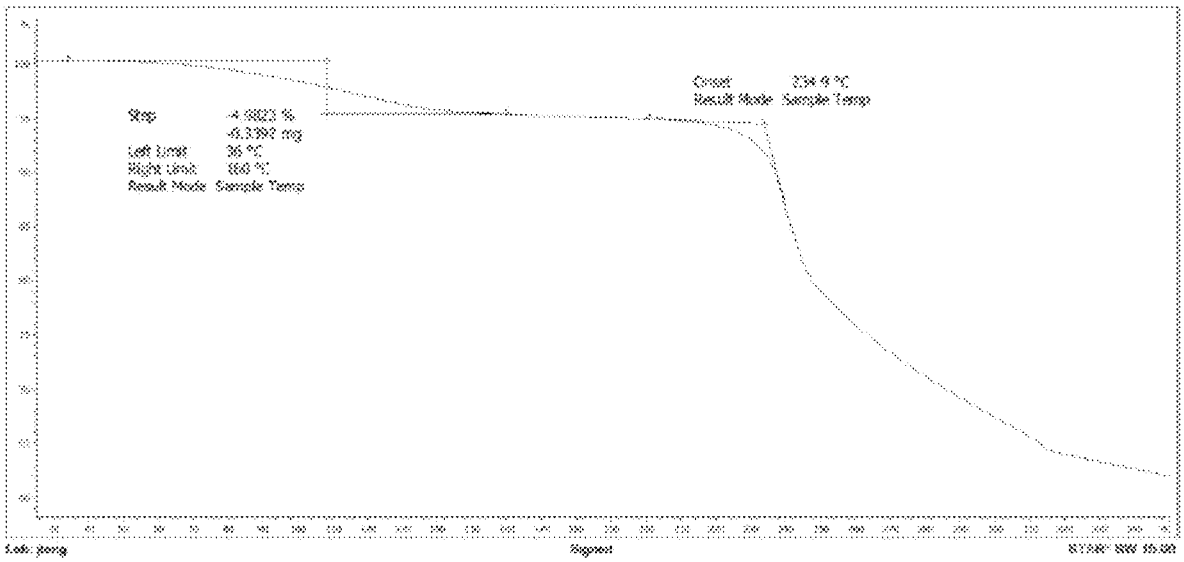
FIG. 14 is a TGA thermogram of the bis-HCl salt of compound of Structural Formula 1—Form D.

The TGA trace of Form D is depicted in FIG. 14.

Weight loss of approximately 5.0% was observed during heating from 36° C. to 160° C. in the TG thermogram.

Figure 15:
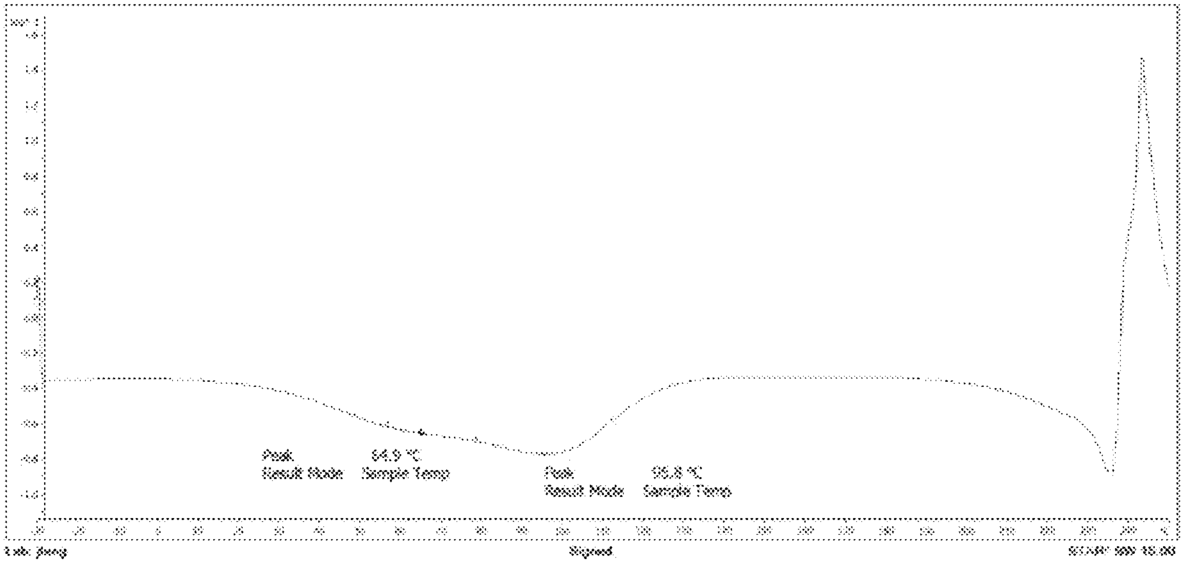
FIG. 15 is a DSC of the bis-HCl salt of compound of Structural Formula 1—Form D.

The DSC trace of Form C is shown in FIG. 15 The DSC thermogram displays a two overlapping broad endothermic peaks at approximately 65° C. and approximately 96° C., followed by large exothermic peak at about 243° C.

Figure 16:
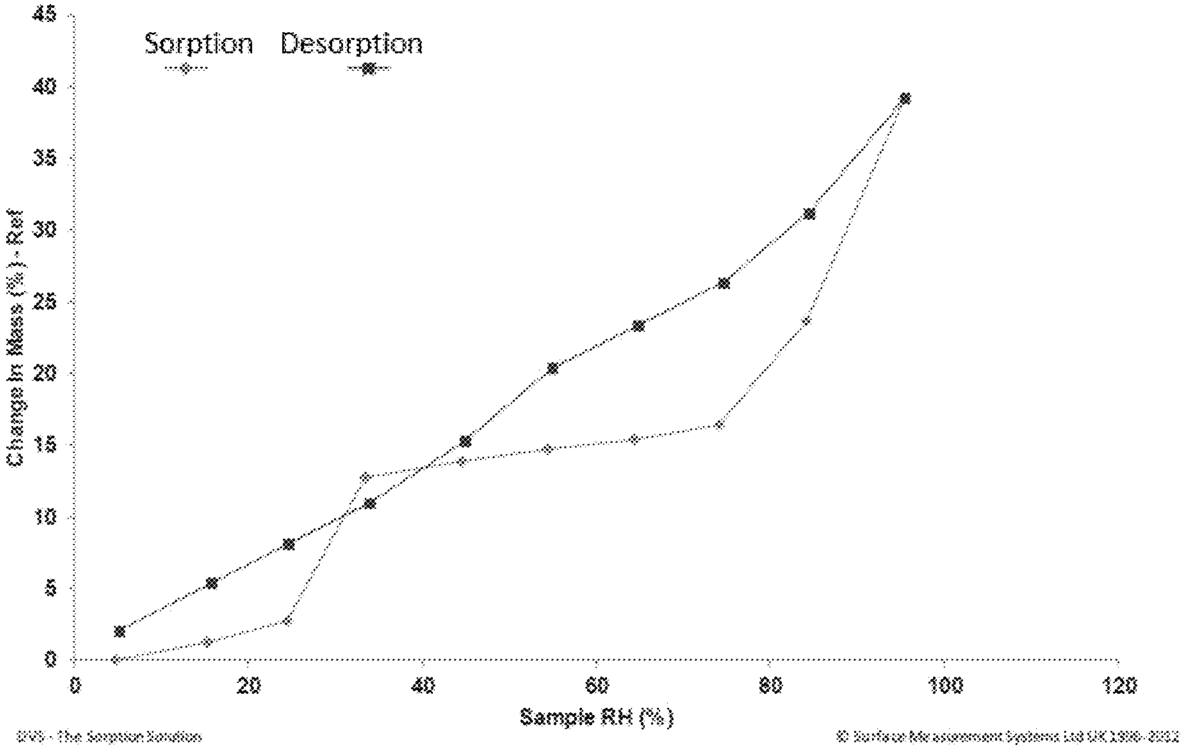
FIG. 16 is a DVS pattern of the bis-HCl salt of compound of Structural Formula 1—Form D.

The DVS pattern of Form C is depicted in FIG. 16. The DVS pattern displays weight gain of about 2.7% in the range of 5-25% RH, followed by a rapid weight gain of about 10% in the range of 25-35% RH, followed by a low weight gain of about 3.7% in the range of 35-75% RH, with a total weight gain of about 39.2% between 5 and 95% RH.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A crystalline form of the bis-HCl salt of a compound represented by Structural Formula 1:

(1)

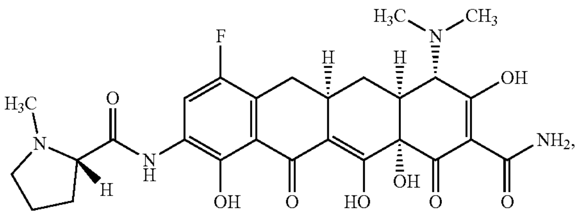

wherein:

the crystalline form is characterized by at least three x-ray powder diffraction peaks at 2θ angles selected from 7.32°, 8.91°, 10.15°, and 10.57°.

2. The crystalline form of claim 1, wherein the crystalline form is characterized by at least four x-ray powder diffraction peaks at 2θ angles selected from 7.32°, 8.91°, 10.15°, 10.57°, 15.47°, and 24.39°, and wherein at least three x-ray powder diffraction peaks are selected from 7.32°, 8.91°, 10.15°, and 10.57°.

3. The crystalline form of claim 1, wherein the crystalline form is characterized by at least five x-ray powder diffraction peaks at 2θ angles selected from 7.32°, 8.91°, 10.15°, 10.57°, 15.47°, 18.12°, 23.17°, 24.39°, and 25.58°, and wherein at least three x-ray powder diffraction peaks are selected from 7.32°, 8.91°, 10.15°, and 10.57°.

4. The crystalline form of claim 1, wherein the crystalline form is characterized by x-ray powder diffraction peaks at 2θ angles of 7.32°, 8.91°, 10.15°, and 10.57°.

5. The crystalline form of claim 1, wherein the crystalline form is characterized by x-ray powder diffraction peaks at 2θ angles of 7.32°, 8.91°, 10.15°, 10.57°, 15.47°, 18.12°, 23.17°, 24.39°, and 25.58°.

6. The crystalline form of claim 1, wherein the crystalline form is characterized by x-ray powder diffraction peaks at 2θ angles of 7.32°, 8.91°, 10.15°, 10.57°, 14.69°, 14.94°, 15.26°, 15.47°, 18.12°, 23.17°, 24.39°, and 25.28°.

7. The crystalline form of claim 1, wherein the crystalline form is characterized by an x-ray powder diffraction pattern substantially in accordance with that depicted in FIG. 1.

8. A crystalline form of the bis-HCl salt of a compound represented by Structural Formula 1:

(1)

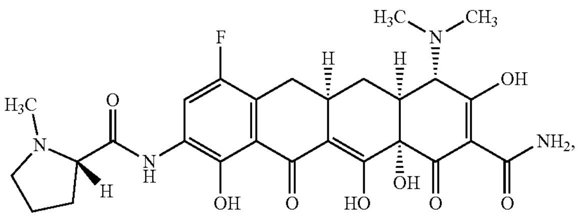

wherein:

the crystalline form is characterized by at least three x-ray powder diffraction peaks at 2θ angles selected from 5.72°, 10.73°, 12.34°, and 16.89°.

9. The crystalline form of claim 8, wherein the crystalline form is characterized by at least four x-ray powder diffraction peaks at 2θ angles selected from 5.72°, 10.73°, 12.34°, 13.46°, 16.89°, and 21.57°, and wherein at least three x-ray powder diffraction peaks are selected from 5.72°, 10.73°, 12.34°, and 16.89°.

10. The crystalline form of claim 8, wherein the crystalline form is characterized by at least five x-ray powder diffraction peaks at 2θ angles selected from 5.72°, 7.30°, 10.73°, 12.34°, 13.46°, 16.89°, 17.73°, 20.47°, and 21.57°, and wherein at least three x-ray powder diffraction peaks are selected from 5.72°, 10.73°, 12.34°, and 16.89°.

11. The crystalline form of claim 8, wherein the crystalline form is characterized by x-ray powder diffraction peaks at 2θ angles of 5.72°, 10.73°, 12.34°, and 16.89°.

12. The crystalline form of claim 8, wherein the crystalline form is characterized by x-ray powder diffraction peaks at 2θ angles of 5.72°, 7.30°, 10.73°, 12.34°, 13.46°, 16.89°, 17.73°, 20.47°, and 21.57°.

13. The crystalline form of claim 8, wherein the crystalline form is characterized by x-ray powder diffraction peaks at 2θ angles of 5.72°, 7.30°, 10.73°, 10.89°, 12.34°, 13.46°, 14.66°, 14.78°, 15.87°, 16.89°, 17.73°, 19.10°, 20.47°, 20.79°, 21.57°, 23.55°, and 24.93°.

14. The crystalline form of claim 8, wherein the crystalline form is characterized by an x-ray powder diffraction pattern substantially in accordance with that depicted in FIG. 5.

15. A crystalline form of the bis-HCl salt of a compound represented by Structural Formula 1:

(1)

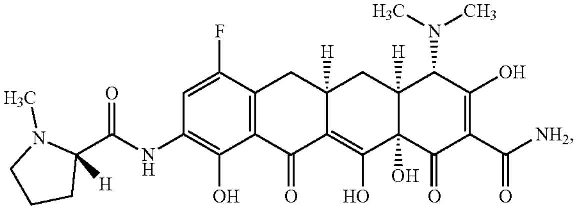

wherein:

the crystalline form is characterized by at least three x-ray powder diffraction peaks at 2θ angles selected from 6.02°, 11.14°, 12.95°, and 18.57°.

16. The crystalline form of claim 15, wherein the crystalline form is characterized by at least four x-ray powder diffraction peaks at 2θ angles selected from 6.02°, 11.14°, 11.44°, 12.95°, and 18.57°, and wherein at least three x-ray powder diffraction peaks are selected from 6.02°, 11.14°, 12.95°, and 18.57°.

17. The crystalline form of claim 15, wherein the crystalline form is characterized by at least five x-ray powder diffraction peaks at 2θ angles selected from 6.02°, 7.62°, 11.14°, 11.44°, 12.95°, 18.57°, 19.76°, 21.55°, 22.40°, and 26.55°, and wherein at least three x-ray powder diffraction peaks are selected from 6.02°, 9.14°, 12.95°, and 18.57°.

18. The crystalline form of claim 15, wherein the crystalline form is characterized by x-ray powder diffraction peaks at 2θ angles of 6.02°, 11.14°, 12.95°, and 18.57°.

19. The crystalline form of claim 15, wherein the crystalline form is characterized by x-ray powder diffraction peaks at 2θ angles of 6.02°, 7.62°, 11.14°, 11.44°, 12.95°, 18.57°, 19.76°, 21.55°, 22.40°, and 26.55°.

20. The crystalline form of claim 15, wherein the crystalline form is characterized by x-ray powder diffraction peaks at 2θ angles of 6.02°, 7.62°, 11.14°, 11.44°, 12.95°, 14.05°, 15.31°, 16.67°, 18.57°, 19.76°, 21.55°, 22.40°, 26.13°, 26.55°, 28.19°.

21. The crystalline form claim 15, wherein the crystalline form is characterized by an x-ray powder diffraction pattern substantially in accordance with that depicted in FIG. 9.

22. A crystalline form of the bis-HCl salt of a compound represented by Structural Formula 1:

(1)

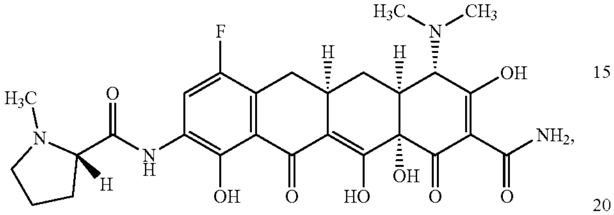

wherein:

the crystalline form is characterized by at least three x-ray powder diffraction peaks at 2θ angles selected from 3.68°, 13.26°, 16.11°, and 16.97°.

23. The crystalline form of claim 22, wherein the crystalline form is characterized by at least four x-ray powder diffraction peaks at 2θ angles selected from 3.68°, 9.78°, 13.26°, 16.11°, and 16.97°, and wherein at least three x-ray powder diffraction peaks are selected from 3.68°, 13.26°, 16.11°, and 16.97°.

24. The crystalline form of claim 22, wherein the crystalline form is characterized by at least five x-ray powder diffraction peaks at 2θ angles selected from 3.68°, 9.78°, 13.26°, 14.76°, 16.11°, 16.97°, 25.94°, and 26.62°, and wherein at least three x-ray powder diffraction peaks are selected from 3.68°, 13.26°, 16.11°, and 16.97°.

25. The crystalline form of claim 22, wherein the crystalline form is characterized by x-ray powder diffraction peaks at 2θ angles of 3.68°, 13.26°, 16.11, and 16.97°.

26. The crystalline form of claim 22, wherein the crystalline form is characterized by at least five x-ray powder diffraction peaks at 2θ angles of 3.68°, 9.78°, 13.26°, 14.76°, 16.11°, 16.97°, 25.94°, and 26.62°.

27. The crystalline form of claim 22, wherein the crystalline form is characterized by x-ray powder diffraction peaks at 2θ angles of 3.68°, 6.39°, 9.78°, 13.26°, 14.26°, 14.76°, 16.11°, 16.97°, 20.65°, 25.94°, and 26.62°.

28. The crystalline form of claim 22, wherein the crystalline form is characterized by an x-ray powder diffraction pattern substantially in accordance with that depicted in any of FIG. 4.

29. A composition, comprising particles of one or more crystalline forms of a compound represented by the bis-HCl salt of Structural Formula 1:

(1)

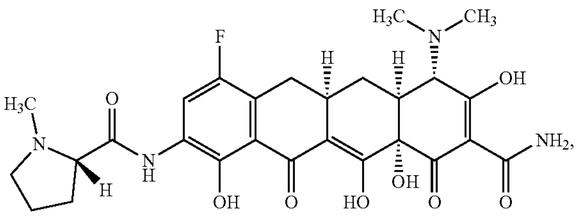

wherein the one or more crystalline forms are selected from:

a crystalline form characterized by at least three x-ray powder diffraction peaks at 2θ angles selected from 7.32°, 8.91°, 10.15°, and 10.57°;

a crystalline form characterized by at least three x-ray powder diffraction peaks at 2θ angles selected from 5.72°, 10.73°, 12.34°, and 16.89°;

a crystalline form characterized by at least three x-ray powder diffraction peaks at 2θ angles selected from 6.03°, 7.62°, 12.89°, and 18.59°; and a crystalline form characterized by at least three x-ray powder diffraction peaks at 2θ angles selected from 3.68°, 13.26°, 16.11°, and 16.97°.

30. A pharmaceutical composition, comprising the crystalline form of the composition of claim 29 and a pharmaceutically acceptable carrier.

31. A method for treating or preventing a tetracycline-responsive disease or disorder, the method comprising administering to a subject in need thereof a therapeutically or prophylactically effective amount of the crystalline form of any one of claims 1-7, 8-21, 22-28, the composition of claim 29, or the pharmaceutical composition of claim 30.

32. The method of claim 31, wherein the tetracycline-responsive disease or disorder is an infection.

33. The method of claim 32, wherein the infection is caused by bacteria.

34. The method of claim 33, wherein the infection is caused by a Gram-positive bacterium.

35. The method of claim 33, wherein the infection is caused by a Gram-negative bacterium.

36. The method of claim 32, wherein the infection is a urinary tract infection.

37. The method of claim 32, wherein the infection is an intra-abdominal infection.

38. The method of claim 31, wherein the tetracycline-responsive disease or disorder is oral mucositis.

39. The method of claim 38 wherein the patient is suffering from head and neck cancer.

40. The method of claim 39, wherein the head and neck cancer is selected from: laryngeal cancer; hypopharyngeal cancer; nasal cavity cancer; paranasal sinus cancer; nasopharyngeal cancer; oral cancer; oropharyngeal cancer; and salivary gland cancer.

* * * * *